United States Patent [19]
Thomas et al.

[11] Patent Number: 6,117,985
[45] Date of Patent: Sep. 12, 2000

[54] ANTIBODY COMPOSITIONS FOR PREPARING ENRICHED CELL PREPARATIONS

[75] Inventors: Terry Thomas; Peter Lansdorp, both of Vancouver, Canada

[73] Assignee: Stemcell Technologies Inc., Vancouver, Canada

[21] Appl. No.: 09/088,227

[22] Filed: Jun. 1, 1998

Related U.S. Application Data

[63] Continuation-in-part of application No. 08/566,295, Dec. 1, 1995, which is a continuation-in-part of application No. 08/491,175, Jun. 16, 1995, Pat. No. 5,877,299.

[51] Int. Cl.$^7$ ..................... A61K 39/395; A61K 35/12; A01N 1/02

[52] U.S. Cl. ............... 530/413; 435/2; 435/372; 530/388.73; 530/388.75; 530/388.7; 424/143.1; 424/145.1; 424/153.1; 424/155.1

[58] Field of Search ................. 530/413, 388.73, 530/388.75, 388.7; 435/2, 372; 424/143.1, 144.1, 153.1, 155.1, 277.1

[56] References Cited

U.S. PATENT DOCUMENTS

| | | |
|---|---|---|
| 4,474,893 | 10/1984 | Reading . |
| 4,722,899 | 2/1988 | Hamaoka et al. . |
| 4,752,582 | 6/1988 | Vanderlaan et al. . |
| 4,868,109 | 9/1989 | Lansdorp . |
| 5,087,570 | 2/1992 | Weissman et al. . |
| 5,137,809 | 8/1992 | Loken et al. . |
| 5,262,319 | 11/1993 | Iwata et al. . |

OTHER PUBLICATIONS

Knapp, W. et al. eds, Oxford University Press. Oxford, pp.818, Civin, C. et al., Report on the CD34 cluster workshop. In: Leucocyte typing IV, White Cell Differentiation Antigens, (1989).
Ishizawa, L. et al., In: Hematopoietic Stem Cells: The Mulhouse Manual eds. Winder, E. et al., 171–182, (1994).
Shpall, E.J., et al., J. of Clinical Oncology, 12:28–36, 1994.
Winslow, J.M., et al., Bone Marrow Transplantation, 14:265–271, 1994.
Thomas, T.E., Cancer Research, Therapy and Control, 4(2): 119–128), 1994.
Linch, D.C. and Nathan, D.G., Nature 312 20/27: 775–777, 1984.
Sieff, C.A., et al., Science 230: 1171–1173, 1985.
Kannourakis, G. and Bol, S., Exp. Hematol, 15:1103–1108, 1987.
Carlo–Stella et al., Blood 84, 10 supple:104a, 1994.
Reading, C., et al., Blood 84, 10supple.:399a, 1994.
Hodgson, G.S. & Bradley, T.R., Nature, vol. 281, pp. 381–382; (Oct. 1979).
Visser et al., J. Exp. Med., vol. 59, pp. 1576–1590, 1984.
Spangrude et al., Science, vol. 241:58–62, 1988.
Szilvassy et al., Blood, 74:930–939, 1989.
Ploemacher, R.E. & Brons, R.H.C., Exp. Hematol., 17:263–266, 1989.
Udomsakdi et al., Exp. Hematol., 19:338, 1991.
Sutherland et al., Proc. Natl. Acad. Sci., 87:3584, 1990.
Craig et al., British Journal of Haematology, 88:24–30, 1994.
Lansdorp, P.Al. and Dragowska, W., J. Exp. Med. 175:1501–1509, 1992.
Sutherland, H.J., et al., Blood 74.1563–1570, 1989.
Van Vlasselaer, P., Density Adjusted Cell Sorting (DACS), A Novel Method to Remove Tumor Cells From Peripheral Blood and Bone Marrow StemCell Transplants. (1995) 3rd International Symposium on Recent Advances in Hematopoietic Stem Cell Transplantation–Clinical Progress, New Technologies and Gene Therapy, San Diego, CA.
Berenson et al., Journal of Immunological Methods 91:11–19, 1986.
Nordon et al., Cytometry 16:25–33, 1994.
Molday, R.S. and MacKenzie, D., J. Immunol. Methods 52:353, 1982.
Thomas et al., J. Hematother. 2:297, 1993.
Thomas, T.E. et al., J. Immunol Methods 154:245;252, 1992.
Lansdorp, P.M. and Thomas, T.E., Mol. Immunol. 27:659–666, 1990.
Thoma et al., Blood, vol. 83(8), 2103–2114, 1994.
van der Schoot et al., Blood, vol. 76(9), 1853–1859, 1990.
Smeland et al., Leukemia, vol. 6(8), 845–852, 1992.
Paul, W.E., Fundamental Immunology, Chapter 8, Raven Press NY, 1993.
Sevier et al., Clinical Chemistry, vol. 27, No. 11, 1797–1806, 1981.
Seaver et al., Genetic Engineering News, vol. 14, No. 14, pp. 10 and 21, 1994.
Gabbianelli et al., Science, vol. 249, 1561–1564, Sep. 1990.
Saeland et al., Exp. Haematol., vol. 20:24–33, 1992.
Verfaillie et al., J. Exp. Med., vol. 172:509–520, Aug. 1990.
Berenson et al., Blood, vol. 67, No. 2, 509–515, Feb. 1986.
Greenwalkt et al., Blood, vol. 80, No. 5, 1105–1115, Sep. 1992.
Penninger et al., Immunol. Review, No. 135, 183–214, 1993.
Fischer et al., J. Immunology, vol. 144, No. 2, 638–641, Jan. 1990.
Kuijpers et al., J. Immunology, vol. 151, No. 9, 4934–4940, Nov. 1993.
Kuijpers et al., J. Cell. Biol., vol. 118, No. 2, 457–466, Jul. 1992.
Hakomori, Ann. Rev. Immunol., vol. 2, 103–126, 1984.
Ross, A.A. et al, ISHAGE '98, Baltimore, J. Hematother 7:1993, No. 3 (P29).

(List continued on next page.)

*Primary Examiner*—Julie Burke
*Attorney, Agent, or Firm*—Bereskin & Parr

[57] ABSTRACT

The present invention relates to antibody composition that are useful in preparing enriched cell preparations such as human hematopoietic progenitor cells and stem cells and non-hematopoietic tumor cells. The invention also relates to kits for carrying out the processes and to the cell preparations prepared by the processes.

11 Claims, 5 Drawing Sheets

OTHER PUBLICATIONS

Shammo, J.M. et al, ISHAGE '98, Baltimore, J. Hematother 7:1993, No. 3 (P128).
Ross, A.A. et al., ISHAGE '98, Baltimore, J. Hematother 7:1993, No. 3 (P131).
Bosnes, M. et al., ISHAGE '98, Baltimore, J. Hematother 7:1993, No. 3 (P138).
Randen, I. et al., ISHAGE '98, Baltimore, J. Hematother 7:1993, No. 3 (P139).
Naume, B. et al., ISHAGE '98, Baltimore, J. Hematother 7:1993, No. 3 (P140).
Krüger, W.H. et al., ISHAGE '98, Baltimore, J. Hematother 7:1993, No. 3 (P137).
Moss et al., Blood, vol. 83, No. 10, 3085–3089, 1994.
Moss, T.J. and Ross, A.A., Journal of Hematotherapy, 1:225–232, 1992.
Brockstein, B.E. et al., Journal of Hematotherapy, 5:617–624, 1996.
Sharp, J.G. et al., Journal of Hematotherapy, 4:141–148, 1995.
Sharp, J.G., Journal of Hematotherapy, 5:519–524, 1996.
Chan, W.C. et al., Journal of Hematotherapy, 3:175–184, 1994.
Passos–Coelho, J.L. et al., Blood, vol. 85, No. 4, 1138–1143, 1995.
Racila, E. et al., Proc. Natl. Acad. Sci. USA, vol. 95, 4589–4594, Apr. 1998.
Moss, T.J. et al., Journal of Hematotherapy, 3:163–164, 1994.
Naume, B. et al. Jounral of Hematotherapy 6:103–114, 1997.
Rye, P.D., et al., American Journal of Pathology, vol. 150, No. 1, 99–106, Jan. 1997.
Denis, M.G. et al., Int. J. Cancer (Pred. Oncol.): 74, 540–544, 1997.
Eaton et al., Short Technical Reports, vol. 22, No. 1, Circle Reader Service No. 191–194, 1997.
Moss, T.J. and Kahn, D.J., Bone Marrow Transplantation, vol. 18, Suppl. 1, S17, 1996.
Moss, T.J., et al. Journal of Hematotherapy, 1:65–73, 1992.
Moss, T.J. et al. ISHAGE '98 Baltimore, J. Hematotherapy 7, No. 3:1998, No. 3 (P133), p. 299.
Clarke, C. et al., Epith Cell Biol 3:38–46, 1994.
Hardingham, J.E. et al. Mol. Med. Nov. 1995; 1(7):789–94, Abstract.
Tedder, T.F. and P.J. Jansen, Current Protocols in Immunology, 7.32.1–7.32.16, 1997.
Schuler, G. et al., Dendritic Cells: Biology and Clinical Applications, Academic Press, Chapter 27. pp. 515–533 (1999).
Metcalfe, D.D., Current Protocols in Immunology, Unit 7.24, pp. 7.24.1 to 7.24.4, 1991.
Swiggard, W.J. et al. Current Protocols in Immunology, Unit 3.7, pp. 3.7.1 to 3.7.11, 1992.

Enriched: 69% CD34$^{bright}$
20% CD34$^{lo}$
60% Recovery of CD34$^+$

Start: 4% CD34$^{bright}$
2% CD34$^{lo}$

*estimated from dilution of pleural effusion

ANTIBODY COMPOSITIONS FOR PREPARING ENRICHED CELL PREPARATIONS

This is a continuation-in-part of U.S. patent application Ser. No. 08/566,295, filed Dec. 1, 1995, which is a continuation-in-part of U.S. patent application Ser. No. 08/491,175, filed Jun. 16, 1995, now U.S. Pat. No. 5,877,299 that issued on Mar. 2, 1999 both of which are incorporated herein by reference in their entirety.

FIELD OF THE INVENTION

The present invention relates to novel antibody compositions, and processes and kits for preparing enriched cell preparations, such as cell preparations enriched in human hematopoietic progenitor cells or stem cells or non-hematopoietic tumor cells.

BACKGROUND OF THE INVENTION

Blood cells have a relatively short life span and need to be replenished throughout life. In adults, blood cell formation or hematopoiesis takes place in the bone marrow, but blood-forming stem cells can also be found in peripheral blood. Hematopoietic cells represent a hierarchy of proliferating and differentiating cells. The most abundant are the differentiating or lineage committed cells. These cells have limited or no proliferative capacity and represent specialized end cells that are found in blood, and their immediate precursors.

The immediate precursors of the differentiating cells are the progenitor cells. Most of these cells are restricted to differentiate along a single lineage but they may have quite extensive proliferative capacity. Progenitor cells appear morphologically as blast cells, and they typically do not have specific features of the hematopoietic lineage to which they are committed.

Progenitor cells are derived from stem cells. Stem cells have been historically defined as cells capable of long term hematopoietic repopulation. This implies their ability to self-renew as well as to generate daughter cells of any of the hematopoietic lineages. The presence of stem and progenitor cells may be detected by their ability to produce colony-forming cells in culture and repopulate xenogeneic hosts such fetal sheep (Zanjani et al., 1994 J. Clin. Invest, Vol. 89, p. 1178–1188) and immuno-deficient mice (Dick et al., 1991 Immunological Reviews, Vol. 124:25–43). They may also be detected by screening for the CD34 antigen which is a positive marker for early hematopoietic cells including colony forming cells and stem cells. At present, the long term culture initiating cell (LTCIC) assay appears to be the best way to detect stem cells, or at least the most primitive progenitor cells, using tissue culture methodologies.

There is a continued interest in developing stem cell purification techniques. Pure populations of stem cells will facilitate studies of hematopoiesis. Transplantation of hematopoietic cells from peripheral blood and/or bone marrow is also increasingly used in combination with high-dose chemo- and/or radiotherapy for the treatment of a variety of disorders including malignant, nonmalignant and genetic disorders. Very few cells in such transplants are capable of long-term hematopoietic reconstitution, and thus there is a strong stimulus to develop techniques for purification of hematopoietic stem cells. Furthermore, serious complications and indeed the success of a transplant procedure is to a large degree dependent on the effectiveness of the procedures that are used for the removal of cells in the transplant that pose a risk to the transplant recipient. Such cells include T lymphocytes that are responsible for graft versus host disease (GVHD) in allogenic grafts, and tumor cells in autologous transplants that may cause recurrence of the malignant growth. It is also important to debulk the graft by removing unnecessary cells and thus reducing the volume of cyropreservant to be infused.

Hematopoietic cells have been separated on the basis of physical characteristics such as density and on the basis of susceptibility to certain pharmacological agents which kill cycling cells. The advent of monoclonal antibodies against cell surface antigens has greatly expanded the potential to distinguish and separate distinct cell types. There are two basic approaches to separating cell populations from bone marrow and peripheral blood using monoclonal antibodies. They differ in whether it is the desired or undesired cells which are distinguished/labeled with the antibody(s).

In positive selection techniques the desired cells are labeled with antibodies and removed from the remaining unlabeled/unwanted cells. In negative selection, the unwanted cells are labeled and removed. Antibody/complement treatment and the use of immunotoxins are negative selection techniques, but FACS sorting and most batch wise immunoadsorption techniques can be adapted to both positive and negative selection. In immunoadsorption techniques cells are selected with monoclonal antibodies and preferentially bound to a surface which can be removed from the remainder of the cells e.g. column of beads, flasks, magnetic particles. Immunoadsorption techniques have won favour clinically and in research because they maintain the high specificity of targeting cells with monoclonal antibodies, but unlike FACSorting, they can be scaled up to deal directly with the large numbers of cells in a clinical harvest and they avoid the dangers of using cytotoxic reagents such as immunotoxins, and complement.

Current positive selection techniques for the purification of hematopoietic stem cells target and isolate cells which express CD34 (approximately 1–2% of normal bone marrow) (Civin, C. l., Trischmann, T. M., Fackler, M. J., Bernstein, I. D., Buhring, H. J., Campos, L. et al. 1989 Report on the CD34 cluster workshop, In: Leucocyte typing IV, White Cell Differentiation Antigens. Knapp, W., Dorken, B., Gilks, W. R., Reiber, E P., Schmidt, R. E., Stein, H., and Kr. von den Borne, A. E. G Eds., Oxford University Press. Oxford, pp.818). Thus, the potential enrichment of hematopoietic stem cells using this marker alone is approximately 50 fold. Available techniques typically recover 30–70% of the CD34$^+$ cells in the start suspension and produce an enriched suspension which is 50–90% CD34$^+$ (Firat et al., 1988, Bone Marrow Transplantation, Vol. 21:933–938; deWynter, E. A. et al., 1975, Stem Cells, Vol. 13:524–532; Shpall, E. J., et al. 1994, J. of Clinical Oncology 12:28–36; Thomas, T. E., 1994, Cancer Research, Therapy and Control 4(2): 119–128). The positive selection procedures suffer from many disadvantages including the presence of materials such as antibodies and/or magnetic beads on the CD34$^+$ cells, and damage to the cells resulting from the removal of these materials. Also to be considered is the recent evidence that some long term repopulating cells are CD34$^-$ (negative) (Zanjani et al., 1998, Exp. Hematol., Vol. 26:353–360) and methods that isolate CD34$^+$ will not capture these cells.

Negative selection has been used to remove minor populations of cells from clinical grafts. These cells are either T-cells or tumor cells that pose a risk to the transplant recipient. The efficiency of these purges varies with the technique and depends on the type and number of antibodies used. Typically, the end product is very similar to the start suspension, missing only the tumor cells or T-cells.

Transplants of purified stem cells without differentiated or lineage committed cells will give short and long-term hematopoietic support (Shpall, E. J., et al. 1994, J. of Clinical Oncology 12:28–36). Since differentiated cells make up a vast majority of the cells in bone marrow and blood, depletion of these cells produces a much smaller cell suspension. The number of cells in the final product and the degree of enrichment of progenitor/stem cells will depend on the efficiency of the antibody targeting and the removal of labeled cells.

There are several studies that enrich for hematopoietic stem cells by depleting lineage committed cells but all require a number of positive or negative selection steps to achieve the desired degree of enrichment (50 fold). Early studies required prior density separation and extensive incubations to remove adherent cells (Linch, D. C, and Nathan, D. G. 1984, Nature 312 20/27: 775–777; Sieff, C. A., et al., 1985, Science 230: 1171–1173; Kannourakis, G. and Bol, S., 1987 Exp. Hematol 15:1103–1108.). More recent techniques are no less cumbersome; involving density separation steps followed by two partial lineage depletions (Winslow, J. M., et al., 1994, Bone Marrow Transplantation 14:265–271) or a partial lineage depletion using panning or FACS followed finally by positive selection using FACS (Carlo-Stella et al. 1994, Blood 84, 10 supple.:104a; Reading, C., et al. (1994), Blood 84, 10 supple.:399a). Most of these methods for lineage depletion lack effective antibody combinations against myeloid cells, erythrocytes and/or B-cells.

U.S. Pat. No. 5,087,570 describes a process for preparing a hematopoietic cell composition using a combination of positive and negative selection. The process relies on the use of antibody to the Sca-1 antigen which is associated with murine clonogenic bone marrow precursors of thymocytes and progeny T-cells. The Sca-1 antibody is not useful in isolating human hematopoietic cells.

Epithelial cancers of the bronchi, mammary ducts and the gastrointestinal and urogenital tracts represent a major type of solid tumors seen today. Micrometastatic tumor cell migration is thought to be an important prognostic factor for patients with epithelial cancer (Vaughan et al., 1990, Proc. Am. Soc. Clin. Oncol. 9:9). Our ability to detect such metastatic cells is limited by the effectiveness of tissue or fluid sampling and the sensitivity of tumor detection methods. From a research point of view, it is also very difficult to study such rare cells and determine the biological changes which enable spread of disease. Metastatic epithelial tumor cells disseminate to distant sites such as bone marrow and lymph nodes. Bone marrow has become an important indicator organ for the spread of epithelial cells because of its easy accessibility and the lack of normal epithelial cells making identification of tumor cells less difficult. The recent trend in autologous transplantation away from the use of bone marrow grafts to cytokine mobilized peripheral blood has raised the question of how often peripheral blood is contaminated with micrometastatic tumor cells. Epithelial tumor contamination in peripheral blood is less frequent than in bone marrow (Ross et al., 1993, Blood, 82(9):2605–2610) but cytokine mobilization may also "mobilize" tumor cells (Brugger et al., 1994, Blood, 83(3):636–640). Both cancer research and patient therapy could benefit from method of enriching epithelial tumor cells from blood, bone marrow and peritoneal and pleural effusions.

The two most poplar methods in research laboratories for the detection of rare epithelial tumor cells are immunocytochemical staining (ICC) and polymerase chain reaction (PCR). PCR detects specific DNA or RNA sequences. ICC methods rely on antibodies to epithelial-specific cytoskeleton and membrane antigens to stain tumor cells. ICC is more widely used clinically and established laboratories with experienced staff are consistently reporting sensitivities of one tumor cell is $10^5$ bone marrow cells (Pantel, 1996, J. of Hematotherapy, 5:359–367). An enrichment of 100 fold or 2 log could increase this sensitivity to one in $10^7$ cells.

There are two approaches to enriching epithelial tumor cells from a suspension of non-epithelial cells such as bone marrow or blood. One can either target the tumor cells for recovery using an epithelial or tumor specific antibodies (positive selection) or target all the non-epithelial (in this case hematopoietic cells) for depletion (negative selection). The problems with the fist approach, positive selection, is that the recovered tumor cells are covered with antibodies and the sites commonly used for immunocytochemical detection are blocked. It is also difficult to positively select cells from samples that have been stored or previously frozen. The non-specific binding of antibodies to cells or of cells to the separation matrix are too high. Negative selection, on the other hand, can deal with clumpy or previously frozen cell suspensions (Thomas et al., 1998, Methods in Enzymology: Signalling Pathways and Gene Regulation in Hematopoietic Cell Growth and Differentiation "Purification of Hematopoietic Stem cells for Further Biological Study", Academic Press) as the recovered cells have not been labelled with antibody. Both currently available epithelial tumor cells enrichment methods are positive selections using cytokeratin specific antibodies or antibodies to Human Epithelial Antigen (HEA) (Miltenyi Biotec Inc. Aubum CA; and Dynal, Skoyen Norway). A negative selection technique that employs antibodies to CD45 has also been reported but enrichments are only 1–2 log and vary with cell source. Van Vlasselaer (U.S. Pat. No. 5,648,223) teaches a procedure for enriching tumor cells in whole blood using cell-trap centrifugation to enrich tumor cells in circulating bodily fluids, by separation based on density. However, the methods taught by Van Vlasselaer require the construction and operation of a cell trap centrifuge tube calibrated to specific gradients of density, osmolality and pH.

In order to successfully utilize circulating bodily fluids for cancer diagnosis, improved methods of enriching the small number of circulating tumor cells are required.

SUMMARY OF THE INVENTION

The present inventors have developed antibody compositions for use in preparing cell preparations enriched for certain cell types such as human hematopoietic stem cells and progenitor cells as well as non-hematopoietic tumor cells found in blood, bone marrow, pleural and peritoneal effusions.

To enrich for hematopoietic stem cells and progenitor cells, the antibodies in the antibody composition are specific for selected markers associated with lineage committed or differentiated cells thereby allowing them to be removed from the cell preparation. In particular, the present inventors have found using a negative selection technique that an antibody composition containing antibodies specific for glycophorin A, CD3, CD24, CD16, and CD14 gives a cell preparation highly enriched for human hematopoietic and progenitor cells. Preferably, the composition additionally includes antibodies to CD56, CD2, CD19, CD66e and/or CD66b. To enrich for early progenitor and stem cells ($CD34^+$, $CD38^-$ cells), the antibody composition also includes antibodies to CD45RA, CD36 and CD38.

The present inventors have shown that the use of the antibody composition of the present invention in a negative selection technique, to prepare a cell preparation which is enriched for hematopoietic stem cells and progenitor cells offers many advantages over conventional techniques. The antibody composition applied in one step to a sample of peripheral blood, bone marrow, cord blood or frozen bone marrow, results in a greater than 50% recovery of human hematopoietic progenitor/stem cells with approximately a 3 log depletion of differentiated cells.

In addition to enriching for hematopoietic progenitor and stem cells, the above-described antibody compositions can be used to deplete tumor cells derived from hematopoietic cells such as B-cell lymphomas or T-cell leukemias. Accordingly, the present invention also provides an antibody composition to enrich for hematopoietic stem cells and progenitor cells and to remove hematopoietic tumor cells. The composition comprises antibodies specific for glycophorin A, CD3, CD24, CD16, and CD14. The composition preferably also includes antibodies to CD2, CD56, CD19, CD66e and/or CD66b.

The present invention also includes an antibody composition to enrich for hematopoietic stem cells and progenitor cells and to remove non-hematopoietic tumor cells. In such an embodiment, the composition also includes antibodies specific for non-hematopoietic antigens expressed on tumor cells, such as antibodies against antigens expressed on the surface of breast and lung carcinoma and neuroblastoma cells. Accordingly, the present invention provides an antibody composition to enrich for hematopoietic stem cells and progenitor cells and to remove tumor cells comprising antibodies specific for glycophorin A, CD3, CD24, CD 16, CD14 and an antigen present on the tumor cells. The antigens on the tumor cells is preferably a non-hematopoietic antigen expressed on the tumor cells.

The present inventors have shown that the purging antibody composition applied in one step to a sample of peripheral blood, bone marrow, or frozen bone marrow containing tumor cells, results in a greater than 50% recovery of human hematopoietic progenitor/stem cells with approximately a 3–5 log depletion of tumor cells.

The high level of enrichment obtained using the antibody compositions of the invention, does not require additional enrichment or tumor purging steps, which would result in loss of, or damage to, progenitor and stem cells. The recovery of $CD34^+$ cells, $CD34^+CD38^+$ cells, colony forming cells, and LTCIC, is also much higher than with conventional multistep techniques.

The present inventors have also developed an antibody composition for use in preparing cell preparations enriched for non-hematopoietic tumor cells, in particular metastatic tumor cells. The composition is useful in the detection of non-hematopoietic tumor cells from blood and bone marrow of patients to aid in the detection of metastatic disease. The tumor-enriching antibody composition contains antibodies specific for selected markers associated with hematopoietic cells. In particular, the present inventors have found using a negative selection technique that an antibody composition containing antibodies specific for glycophorin A, CD2, CD14, CD16, CD38, CD45 and CD66b, and optionally CD3, CD36, CD56, and/or CD66e, gives a cell preparation highly enriched for non-hematopoietic tumor cells. The present inventors have shown that the tumor enriching antibody compositions applied in one step to a sample of peripheral blood, frozen peripheral blood, bone marrow or pleural or peritoneal effusions containing tumor cells results at least a 2 log enrichment (and typically greater than 3 log enrichment), of the tumor cells.

The enrichment and recovery of human hematopoietic progenitor and stem cells as well as non-hematopoietic tumor cells using the antibody compositions of the invention in a negative selection technique has many advantages over conventional positive selection techniques. As mentioned above, highly enriched cell preparations can be obtained using a single step. The cells obtained using the antibody composition of the invention are not labeled or coated with antibodies or modified making them highly suitable for many uses. For example, the isolated hematopoietic stem cells and progenitor cells can be used in transplantation and other therapeutic uses. The isolated metastatic tumor cells can be used to detect metastatic disease in blood and bone marrow as well as pleural and peritoneal effusions.

The present invention also relates to a negative selection process for enriching and recovering human hematopoietic progenitor cells and stem cells in a sample containing human hematopoietic differentiated, progenitor, and stem cells comprising (a) reacting the sample with an antibody composition containing antibodies capable of binding to the antigens glycophorin A, CD3 CD24, CD16, and CD14, and optionally CD2, CD56, CD19, CD66e and/or CD66b under conditions permitting the formation of conjugates between the antibodies and cells in the sample having the antigens glycophorin A, CD3 CD24, CD16, and CD14, and optionally CD2, CD56, CD19, CD66e and/or CD66b on their surfaces; (b) removing the conjugates, and (c) recovering a cell preparation which is enriched in human hematopoietic progenitor cells and stem cells.

The present invention further provides a negative selection process for enriching and recovering normal human hematopoietic progenitor cells and stem cells and depleting hematopoietic tumor cells in a sample containing human hematopoietic differentiated, progenitor, and stem cells, and hematopoietic tumor cells comprising (a) reacting the sample with an antibody composition containing antibodies capable of binding to the antigens glycophorin A, CD3, CD24, CD16, CD14, and optionally CD2, CD56, CD19, CD66e and/or CD66b, under conditions so that conjugates are formed between the antibodies and the cells in the sample having the antigens glycophorin A, CD3 CD24, CD16, and CD14, and optionally CD2, CD56, CD19, CD66e and/or CD66b; (b) removing the conjugates; and (c) recovering a cell preparation which is enriched in normal human hematopoietic progenitor cells and stem cells and depleted in hematopoietic tumor cells.

The present invention further provides a process for enriching and recovering human hematopoietic stem cells and progenitor cells and depleting tumor cells in a sample containing differentiated cells, progenitor cells, stem cells and tumor cells, comprising (a) reacting the sample with an antibody composition containing antibodies capable of binding to the antigens glycophorin A, CD3 CD24, CD16, and CD14, and an antigen present on the tumor cells and optionally CD2, CD56, CD19, CD66e and/or CD66b under conditions permitting the formation of conjugates between the antibodies and cells in the sample having the antigens glycophorin A, CD3 CD24, CD16, and CD14, and an antigen present on the tumor cells and optionally CD2, CD56, CD19, CD66e and/or CD66b on their surfaces; (b) removing the conjugates; and (c) recovering a cell preparation which is enriched in human hematopoietic progenitor cells and stem cells and depleted in tumor cells.

The present invention also contemplates a negative selection process for enriching for non-hematopoietic metastatic tumor cells in a sample containing the tumor cells and hematopoietic cells comprising (a) reacting the sample with an antibody composition comprising antibodies specific for glycophorin A, CD2, CD14, CD16, CD38, CD45 and CD66b, and optionally CD3, CD36, CD56 and/or CD66e under conditions so that conjugates are formed between the antibodies and hematopoietic cells in the sample expressing the antigens glycophorin A, CD2, CD14, CD16, CD38, CD45 and CD66b, and optionally CD3, CD36, CD56 and/or CD66e; (b) removing the conjugates; and (c) recovering a cell preparation enriched in the tumor cells.

The present invention also relates to a kit useful in preparing a cell preparation enriched in human hematopoietic progenitor and stem cells comprising antibodies specific for glycophorin A, CD3, CD24, CD16, and CD14, and instructions for preparing a cell preparation enriched in hematopoietic progenitor and stem cells.

The present invention further includes a kit useful in preparing a cell preparation enriched in hematopoietic stem cells and progenitor cells and depleted in hematopoietic tumor cells comprising antibodies specific for glycophorin A, CD3, CD24, CD16, and CD14 and instructions for preparing a cell preparation enriched in hematopoietic stem cells and progenitor cells and depleted in hematopoietic tumor cells.

The present invention also includes a kit useful in preparing a cell preparation enriched in hematopoietic stem cells and progenitor cells and depleted in tumor cells comprising antibodies specific for glycophorin A, CD3, CD24, CD16, CD14, and an antigen present on the tumor cells and instructions for preparing a cell preparation enriched in hematopoietic stem cells and progenitor cells and depleted in tumor cells.

The present invention also relates to a kit useful in preparing a cell preparation enriched in non-hematopoietic tumor cells from blood, bone marrow, pleural or peritoneal effusions, comprising antibodies specific for glycophorin A, CD2, CD14, CD16, CD38, CD45 and CD66b, and instructions for preparing a cell preparation enriched in non-hematopoietic tumor cells.

The invention further relates to cell preparations obtained in accordance with the process of the invention. The invention still further contemplates a method of using the antibody compositions of the invention in negative selection methods to recover a cell preparation which is enriched in human hematopoietic progenitor and stem cells or non-hematopoietic tumor cells.

These and other aspects of the present invention will become evident upon reference to the following detailed description and attached drawings. In addition, reference is made herein to various publications, which are hereby incorporated by reference in their entirety.

BRIEF DESCRIPTION OF THE DRAWINGS

The invention will now be described with reference to the accompanying drawings, in which.

DETAILED DESCRIPTION OF THE INVENTION

I. HEMATOPOIETIC CELL TYPES AND TUMOR CELLS

Figure 1:
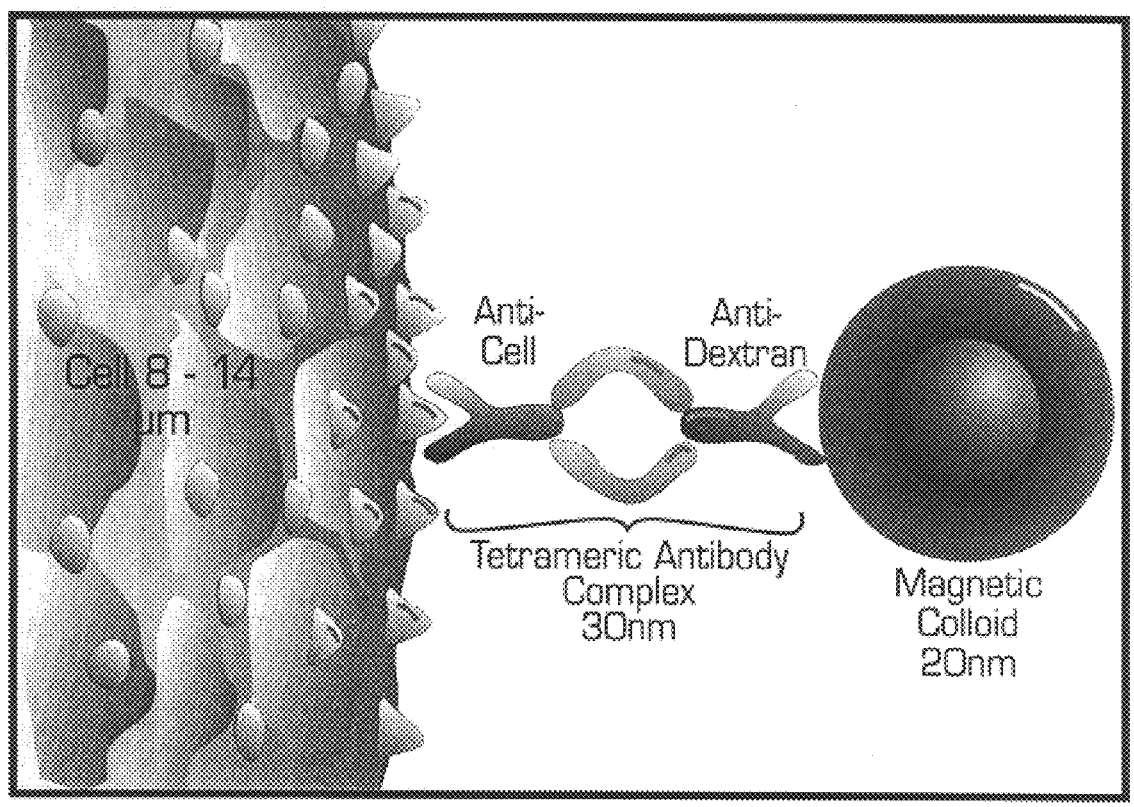
FIG. 1 is a schematic representation of magnetic cell labeling using tetrameric antibody complexes and colloidal dextran iron.

The term "differentiated cells" used herein refers to human hematopoietic cells which have limited or no proliferative capacity. Differentiated cells represent specialized end cells that are found in blood, and their immediate precursors.

The term "progenitor cells" used herein refers to cells which are the immediate precursors of the differentiating cells. Most of the progenitor cells differentiate along a single lineage but they may have quite extensive proliferative capacity. Progenitor cells appear morphologically as blast cells, and they typically do not have specific features of the hematopoietic lineage to which they are committed.

The term "stem cells" used herein refers to the cells from which progenitor cells are derived. Stem cells are defined by their ability to self-renew as well as to generate daughter cells of any of the hematopoietic lineages. Stem cells with long term hematopoietic reconstituting ability can be distinguished by a number of physical and biological properties from differentiated cells and progenitor cells (Hodgson, G. S. & Bradley, T. R., Nature, Vol. 281, pp. 381–382; Visser et al., 1984, J. Exp. Med., Vol. 59, pp. 1576–1590; Spangrude et al., 1988, Science, Vol. 241, pp. 58–62; Szilvassy et al., 1989, Blood, Vol. 74, pp. 930–939; Ploemacher, R. E. & Brons, R. H. C., 1989, Exp. Hematol., Vol. 17, pp.263–266).

The presence of stem cells and progenitor cells in a cell preparation may be detected by their ability to produce colony-forming cells in culture or to repopulate xeonogenic hosts such as immunodeficient mice. They may also be detected by screening for the CD34 antigen which is a positive marker for early hematopoietic cells including colony forming cells and stem cells. Primitive hematopoietic stem cells with long term hematopoietic reconstituting ability can be identified by determining the number of clonogenic cells present after 5 to 8 weeks in long term cultures (Sutherland et al., 1986, Blood, Vol. 74, p. 1563; Udomsakdi et al., 1991, Exp. Hematol., Vol. 19, p. 338; and, Sutherland et al., 1990, Proc. Natl. Acad. Sci., Vol. 87, p. 3584).

Tumor cells which may be removed from a sample using the antibody compositions and processes described herein include tumor cells which have non-hematopoietic antigens or markers expressed on their surfaces i.e. antigens that distinguish the tumor cells from hematopoietic progenitor cells and stem cells. For example, specific markers have been found to be expressed on tumor cells such as breast and lung carcinoma, and neuroblastoma. Table 4 lists specific examples of antibodies which recognize non-hematopoietic antigens expressed on tumor cells.

Some metastatic tumor cells express hematopoietic lineage markers or antigens, for example, tumor cells from B-lymphomas, multiple myeloma, some chronic lymphocytic leukemias (CLL), and some acute lymphocytic leukemias (ALL) express B-cell markers such as CD22, CD20, CD29, and T cells from ALL and CLL express T-cell markers, and antibodies to these antigens may be included in the antibody compositions of the invention to remove tumor cells expressing the hematopoietic lineage antigens.

Tumor cells which may be enriched in a sample using the antibody compositions and processes described herein include non-hematopoietic tumor cells which do not express hematopoietic lineage markers. Non-hematopoietic tumors include epithelial cancers of the bronchi, mammary ducts, gastrointestinal tract, reproductive system and urogenital tract such as carcinomas of the lung, breast, colon, prostate, bladder, ovary, endometrium, cervix, pancreas, oesophagus, small bowel, rectum, uterus, stomach, larynx, skin and vagina.

II. ANTIBODY COMPOSITIONS

As hereinbefore mentioned, the invention relates to an antibody compositions for preparing enriched cell preparations. In one aspect, the antibody composition is for enriching human hematopoietic progenitors and stem cells and comprises antibodies specific for the antigens glycophorin a, CD3, CD24, CD16, and CD14, which are present on the surface of human differentiated cells. In a preferred embodiment, the antibody composition further includes antibodies to CD2, CD56, CD19, CD66e and/or CD66b. The composition may also include antibodies to CD45RA, CD38, and/or CD36.

The antibody composition foe enriching for human hematopoietic progenitor and stem cells may be generally referred to as the "progenitor enrichment composition" or the "progenitor enrichment cocktail". One skilled in the art will appreciate that in addition to the antibodies listed above, the progenitor enrichment cocktail may additionally include other antibodies that are specific for antigens on the surface of differentiated cells including those listed in Table 2. The selection of the antibodies can depend on many factors including the nature of the sample to be enriched. In an embodiment of the invention, an antibody composition is provided for enriching and recovering human hematopoietic progenitor and stem cells from fresh bone marrow consisting of antibodies specific for glycophorin A, CD3, CD24, CD16, CD14, CD66e and CD66b. In a second embodiment, an antibody composition is provided for enriching and recovering human hematopoietic progenitor and stem cells from previously frozen bone marrow consisting of antibodies specific for glycophorin A, CD3, CD24, CD16, and CD14. In a further embodiment of the invention, an antibody composition is provided for enriching and recovering human hematopoietic progenitor and stem cells from peripheral or cord blood consisting of antibodies specific for glycophorin A, CD3, CD24, CD16, CD14, CD66e, CD66b, CD56, CD2 and CD19.

Pluripotent stem cells and committed progenitors express CD34, and this CD34 compartment can be subdivided using antibodies to a variety of cell surface markers. Stem cells co-purify in a population of CD34$^+$ cells which lack or have low expression of certain lineage markers (CD38, CD33, CD45RA, CD71, CD36 and HLA-DR) (Craig et al. 1994, British Journal of Haematology, 88:22–30; Lansdorp, P. A. I. and Dragowska, W. 1992 J. Exp. Med. 175:1501–1509; Sutherland, H, J., et al. 1989 Blood 74.1563–1570). Antibodies recognizing these antigens can be included in the antibody composition to further enrich for stem cells, while losing some of the committed mature CD34$^+$ cells. Preferably, anti-CD45RA, anti-CD38 and anti-CD36 are included in the antibody composition. Accordingly, in another embodiment the present invention provides an antibody composition for enriching for early progenitor cells comprising antibodies specific for glycophorin A, CD3, CD24, CD16, CD14, CD2, CD56, CD19, CD66b, CD45RA, CD36 and CD38.

In another aspect, the present invention also relates to an antibody composition for enriching and recovering human hematopoietic progenitor and stem cells and depleting hematopoietic tumor cells comprising antibodies specific for glycophorin A, CD3, CD24, CD16 and CD14. In a preferred embodiment the antibody composition further includes antibodies to CD2, CD56, CD19, CD66e and/or CD66b.

The present invention also includes an antibody composition for enriching and recovering hematopoietic stem cells and progenitor cells and depleting non-hematopoietic tumor cells. In such an embodiment, the composition also includes antibodies specific for non-hematopoietic antigens expressed on tumor cells, such as antibodies against antigens expressed on the surface of breast and lung carcinoma and neuroblastoma cells. The antibodies to the tumor antigens may be obtained from commercial sources or prepared using techniques known in the art. Preferably, the antibodies specific for non-hematopoietic antigens are specific for antigens expressed on breast and lung carcinoma and neuroblastoma cells, for example a shown in Table 4.

In a further aspect, the invention also includes an antibody composition for enriching and recovering non-hematopoietic tumor cells from blood, bone marrow, pleural and peritoneal effusions comprising antibodies specific for glycophorin A, CD2, CD14, CD16, CD38, CD45 and CD66b, and optionally CD3, CD36, CD56 and/or CD66e.

Within the context of the present invention, antibodies are understood to include monoclonal antibodies and polyclonal antibodies, antibody fragments (e.g., Fab, and F(ab')$_2$) and chimeric antibodies. Antibodies are understood to be reactive against a selected antigen on the surface of a differentiated cell or tumor cell if they bind with an appropriate affinity (association constant), e.g. greater than or equal to $10^7$ M$^{-1}$.

Polyclonal antibodies against selected antigens on the surface of differentiated cells or tumor cells may be readily generated by one of ordinary skill in the art from a variety of warm-blooded animals such as horses, cows, various fowl, rabbits, mice, hamsters, or rats. For example, a mammal, (e.g., a mouse, hamster, or rabbit) can be immunized with an immunogenic form of an antigen which elicits an antibody response in the mammal. Techniques for conferring immunogenicity on an antigen include conjugation to carriers or other techniques well known in the art. For example, the antigen can be administered in the presence of adjuvant. The progress of immunization can be monitored by detection of antibody titers in plasma or serum. Following immunization, antisera can be obtained and polyclonal antibodies isolated from the sera.

Monoclonal antibodies are preferably used in the antibody compositions of the invention. Monoclonal antibodies specific for selected antigens on the surface of differentiated cells or tumor cells may be readily generated using conventional techniques. For example, monoclonal antibodies may be produced by the hybridoma technique originally developed by Kohler and Milstein 1975 (Nature 256, 495–497; see also U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988). Other techniques may also be utilized to construct monoclonal antibodies (for example, see William D. Huse et al., 1989, "Generation of a Large Combinational Library of the Immunoglobulin Repertoire in Phage Lambda," Science 246:1275–1281, L. Sastry et al., 1989 "Cloning of the Immunological Repertoire in *Escherichia coli* for Generation of Monoclonal Catalytic Antibodies: Construction of a Heavy Chain Variable Region-Specific cDNA Library," Proc Natl. Acad. Sci USA 86:5728–5732; Kozbor et al., 1983 Immunol. Today 4, 72 re the human B-cell hybridoma technique; Cole et al. 1985 Monoclonal Antibodies in Cancer Therapy, Allen R. Bliss, Inc., pages 77–96 re the EBV-hybridoma technique to produce human monoclonal antibodies; and see also Michelle Alting-Mees et al., 1990 "Monoclonal Antibody Expression Libraries: A Rapid Alternative to Hybridomas," Strategies in Molecular Biology 3:1–9). Hybridoma cells can be screened immunochemically for production of antibodies specifically reactive with an antigen, and monoclonal antibodies can be isolated.

The term "antibody" as used herein is intended to include antibody fragments which are specifically reactive with specific antigens on the surface of differentiated cells or tumor cells. Antibodies can be fragmented using conventional techniques and the fragments screened for utility in the same manner as described above for whole antibodies. For example (F(ab')$_2$ fragments can be generated by treating antibody with pepsin. The resulting F(ab')$_2$ fragment can be treated to reduce disulfide bridges to produce Fab' fragments.

The invention also contemplates chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes selected antigens on the surface of differentiated cells or tumor cells. See, for example, Morrison et al., 1985; Proc. Natl. Acad. Sci. U.S.A. 81,6851; Takeda et al., 1985, Nature 314:452; Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B.

Antibodies against selected antigens on the surface of differentiated cells or tumor cells may also be obtained from commercial sources as illustrated in Tables 2 and 4.

Antibodies may be selected for use in the antibody composition of the invention based on their ability to deplete targeted differentiated cells and/or tumor cells and recover non-targeted cells (i.e. normal progenitor and stem cells, or specific differentiated cells) in magnetic cell separations as more particularly described herein, and in U.S. Pat. No. 5,514,340, which is incorporated in its entirety herein by reference. In general, an antibody is selected that gives greater than 3 log depletion of differentiated cells or tumor cells, with greater than 75% recovery of CD34$^+$ cells (bone marrow, mobilized blood and cord blood) or non-targeted lymphocytes (steady state blood), in test magnetic cell separations as described herein.

The anti-glycophorin A antibodies contained in the antibody composition of the invention are used to label erythrocytes. Examples of monoclonal antibodies specific for glycophorin A are 2B7.1. (Stem Cell Technologies), 10F7MN (U.S. Pat. No. 4,752,582, Cell lines: ATCC accession numbers HB-8162), and D2.10 (Immunotech, Marseille, France). The concentration of antiglycophorin A antibodies used in the antibody composition are generally less than the concentration that will cause agglutination (i.e. 3–10 µg/ml). Preferably the concentration of antiglycophorin A antibodies used in the antibody composition is between about 0.5 to 5 µg/ml, preferably 1 to 2 µg/ml.

Monoclonal antibodies against CD24, CD3, CD19, CD20, CD22, CD29, CD56, CD2 in the antibody composition of the invention are used to label B and T lymphocytes and NK cells. Examples of monoclonal antibodies specific for CD24, CD3, CD19, CD20, CD22, CD56, and CD2, are 32D12 (Dr. Steinar Funderud, Institute for Cancer Research, Dept. of Immunology, Oslo, Norway,) and ALB9 (Immunotech, Marseille, France); UCHT1 (Immunotech, Marseille, France) and SK7 (Becton Dickinson, Mountain View, Calif.); J4.119 (immunotech, Marseille, France) and Leu-12 (Becton Dickinson, Mountain View, Calif.); MEM97 (Dr. Horejsi, Institute of Molecular Genetics Academy of Sciences of the Czech Republic, Praha, Czech Republic, or Cedarlane Laboratories, Hornby, Ontario, Canada) and Leu-16 (Becton Dickinson, Mountain View, Calif.); SJ10.1H11 (Immunotech, Marseille, France); T199 (Immunotech, Marseille, France); and 6F10.3 (Immunotech, Marseille, France), respectively. The concentration of each of the monoclonal antibodies against CD24, CD3, CD19, CD20, CD56, CD2 contained in the antibody composition is between about 0.5 to 6 µg/ml, preferably 2 to 3 µg/ml.

Monoclonal antibodies against CD14, CD16, CD66e and CD66b in the antibody compositions of the invention are used to label monocytes and granulocytes. Examples of monoclonal antibodies specific for CD14, CD16, CD66e and CD66b, are MEM15 and MEM18 (Dr. Vaclav Horejsi, Institute of Molecular Genetics Academy of Sciences of the Czech Republic, Praha, Czech Republic; Cedarlane Laboratories, Hornby, Ontario, Canada); MEM154 (Dr. Vaclav Horejsi, Institute of Molecular Genetics Academy of Sciences of the Czech Republic, Praha, Czech Republic; Cedarlane Laboratories, Hornby, Ontario, Canada), Leu-11a (Becton Dickinson, Mountain View, Calif.), and 3G8 (Immunotech, Marseille, France); CLB/gran10 (CLB, Central Laboratory of the Netherlands, Red Cross Blood Transfusion Service); and, B13.9 (CLB, Central Laboratory of the Netherlands, Red Cross Blood Transfusion Service) and 80H3 (Immunotech, Marseille, France), respectively. The concentration of each of the monoclonal antibodies against CD14, CD16, CD66e and CD66b contained in the antibody composition is between about 0.5 to 6 µg/ml, preferably 2–3 µg/ml.

Monoclonal antibodies against CD45RA, CD38 and CD36 are used to label T-cells, B-cells plasma cells, granulocytes, platelets, monocytes, differentiated erythroid precursors, and some committed mature progenitors, to further enrich for stem cells. Examples of monoclonal antibodies against CD45RA, CD38 and CD36 are 8D2.2 (Stem Cell Technologies, Vancouver, Canada, Craig et al., 1994, British Journal of Haematology, 88:24–30.), Leu-18 (Becton Dickinson, Mountain View, Calif.); T16 (Immunotech, Marseille, France); and, FA60152 (Immunotech, Marseille, France) and IVC7 (CLB, Central Laboratory of the Netherlands Red Cross Blood Transfusion Service), respectively. The concentration of each of the monoclonal antibodies against CD45RA and CD36 contained in the antibody composition is between about 0.5 to 5 µg/ml, preferably 1 to 3 µg/ml.

Table 2 sets out the most preferred monoclonal antibodies specific for differentiated cells, their sources and concentrations, for use in the antibody compositions of the invention. Table 4 sets out the most preferred monoclonal antibodies specific for tumor cells, and commercial sources/references for the antibodies.

In one embodiment of the invention the antibody composition for enriching for hematopoietic stem cells and progenitor cells, comprises 2B7.1 (glycophorin A), SK7 (CD3), 32D12 (CD24), MEM54 (CD16), and MEM15 (CD14).

In another embodiment of the invention the antibody composition for enriching for hematopoietic stem cells and progenitor cells, comprises 2B7.1 (glycophorin A), SK7 (CD3), 32D12 (CD24), MEM54 (CD16), MEM15 (CD14), 6F10.2 (CD2), T199 (CD56), J4.119 (CD19) and/or 80H3 (CD66b).

In further embodiment of the invention the antibody composition for enriching for early hematopoietic stem and progenitor cells comprises the monoclonal antibodies designated 2B7.1 (glycophorin A), SK7 (CD3), MEM15 (CD14), MEM154 (CD16), 32D12 (CD24), 80H3 (CD66b), J4.119 (CD19), 6F10.3 (CD2), MY31 (CD56), 8D2.2 (CD45RA), T16 (CD38) and FA60152 (CD36), or comprises the monoclonal antibodies designated 10F7MN (glycophorin A), UCHT1 (CD3), ALB9 (CD24), 3G8 (CD16), MEM15 (CD14), B13.9 (CD66b), T199 (CD56), 6F10.3 (CD2), J4.119 (CD19), 8D2.2 (CD45RA), T16 (CD38) and 1VC7 (CD36).

A preferred antibody composition for removing differentiated hematopoietic cells and breast and lung carcinoma cells from a sample comprises the monoclonal antibodies 2B7.1 (glycophorin A), SK7 (CD3), MEM15 (CD14), 3G8 (CD16), ALB9 (CD24), 80H3 (CD66b), J4.119 (CD19), 6F10.3 (CD2), MY31 (CD56), or the monoclonal antibodies 10F7MN (glycophorin A), SK7 (CD3), 32D12 (CD24), MEM154 (CD16), MEM15 (CD14), 80H3 (CD66b) or B13.9 (CD66b), T199 (CD56), 6F10.3 (CD2), J4.119 (CD19), and one or more of the monoclonal antibodies specific for an antigen on the surface of a breast or lung carcinoma as set forth in Table 4. Most preferably the monoclonal antibodies specific for an antigen on the surface of cells from a breast carcinoma used in a composition of the invention are one or more of 5E11, H23A, 6E7, RAR, BerEp4 and BRST1.

Preferred antibody compositions for enriching for non-hematopoietic metastatic tumor cells from a sample containing hematopoietic cells and non-hematopoietic metastitic tumor cells comprise the monoclonal antibodies 2B7.1 (glycophorin A); MEM15 (CD14); 3G8 (CD16); 80H3 (CD66b); 6F10.3 (CD2); T16 (CD38); and MEM28 (CD45).

Antibody compositions in accordance with the present invention may be prepared which lack antibodies to a specific differentiated cell type or lineage committed cell. For example, an antibody composition may be prepared which does not contain antibodies to the CD14, and CD16 antigens which are expressed on monocytes. This composition may be used to prepare a cell preparation which is enriched for monocytes. Other examples of antibody compositions which can be used to prepare cell populations enriched for monocytes, B-cells, T-cells, CD4$^+$T-cells, CD8$^+$ T-cells, and NK cells are set out in Table 3.

III. PROCESS FOR PREPARING ENRICHED CELL PREPARATIONS

The antibody compositions of the invention may be used to enrich and recover cell preparations enriched in a specific cell type such as stem cells and progenitor cells or non-hematopoietic tumor cells. In accordance with a process of the invention, a sample is reacted with an antibody composition containing antibodies which are specific for selected antigens on the surface of the cells to be removed from the sample and not on the cells to be enriched in the sample, under suitable conditions, conjugates form between the antibodies contained in the antibody composition and the cells in the sample containing the antigens on their surface; and the conjugates are removed to provide a cell preparation enriched in specific cells.

(a) Progenitor Cell Enrichment

In one aspect the present invention provides a negative selection process for enriching and recovering human hematopoietic progenitor cells and stem cells in a sample containing human hematopoietic differentiated, progenitor, and stem cells comprising (a) reacting the sample with an antibody composition containing antibodies capable of binding to the antigens glycophorin A, CD3 CD24, CD16, and CD14 under conditions so that conjugates are formed between the antibodies and cells in the sample containing the antigens glycophorin A, CD3 CD24, CD16, and CD14 on their surfaces; (b) removing the conjugates; and, (c) recovering a cell preparation which is enriched in human hematopoietic progenitor cells and stem cells.

The antibody composition for enriching for progenitor and stem cells may additionally include other antibodies specific for antigens on differentiated cells such as CD2, CD56, CD19, CD66e and/or CD66b. The selection of antibodies can largely depend on the nature of the sample to be enriched. When the sample is fresh bone marrow, the composition preferably comprises antibodies to glycophorin A, CD3, CD24, CD16, CD14, CD66e and CD66b. When the sample is mobilized peripheral blood or cord blood, the composition preferably comprises glycophorin A, CD3, CD24, CD16, CD14, CD66e, CD66b, CD56, CD2, and CD19. To enrich for early progenitor cells the composition preferably includes glycophorin A, CD3, CD24, CD16, CD14, CD66e, CD66b, CD56, CD2, CD19, CD45RA, CD36 and CD38.

The inventors have demonstrated that their method of progenitor enrichment provides a cell preparation with greater than 50% recovery of progenitor and stem cells and 3 long depletion of differentiated cells.

(b) Tumor Cell Depletion

In another aspect, the present invention provides a negative selection process for enriching and recovering normal human hematopoietic progenitor cells and stem cells and depleting hematopoietic tumor cells in a sample containing human hematopoietic differentiated, progenitor, and stem cells, and tumor cells comprising (a) reacting the sample with an antibody composition containing antibodies capable of binding to the antigens glycophorin A, CD3, CD24, CD16, and CD14, under conditions so that conjugates are formed between the antibodies and the cells in the sample having the antigens glycophorin A, CD3 CD24, CD16 and CD14; (b) removing the conjugates; and (c) recovering a cell preparation which is enriched in normal human hematopoietic progenitor cells and stem cells and depleted in hematopoietic tumor cells.

The present invention further provides a process for enriching and recovering human hematopoietic stem cells and progenitor cells and depleting tumor cells in a sample containing differentiated cells, progenitor cells, stem cells and tumor cells, comprising (a) reacting the sample with an antibody composition containing antibodies capable of binding to the antigens glycophorin A, CD3 CD24, CD16, and CD14, and an antigen present on the tumor cells and optionally CD2, CD56, CD19, CD66e and/or CD66b under conditions permitting the formation of conjugates between the antibodies and cells in the sample having the antigens glycophorin A, CD3 CD24, CD16, and CD14, and an antigen present on the tumor cells and optionally CD2, CD56, CD19, CD66e and/or CD66b on their surfaces; (b) removing the conjugates; and (c) recovering a cell preparation which is enriched in human hematopoietic progenitor cells and stem cells and depleted in tumor cells.

The inventors have demonstrated that the method of tumor cell depletion provides a cell preparation with a 3 log depletion of tumor cells.

(c) Tumor Cell Enrichment

In another aspect, the present invention provides a negative selection process for enriching for non-hematopoietic metastatic tumor cells in a sample containing the tumor cells and hematopoietic cells comprising (a) reacting the sample with an antibody composition comprising antibodies specific for glycophorin A, CD2, CD14, CD16, CD38, CD45 and CD66b under conditions so that conjugates are formed between the antibodies and hematopoietic cells in the sample expressing the antigens glycophorin A, CD2, CD14, CD16, CD38, CD45 and CD66b; (b) removing the conjugates; and (c) recovering a cell preparation enriched in the tumor cells.

In one embodiment, the tumor cells are metastatic tumor cells derived from epithelial cancers of the bronchi, mammary ducts, reproductive system, gastrointestinal tract and urogenital tract such as lung carcinoma, breast carcinoma, colon carcinoma, prostate carcinoma and bladder carcinoma.

The inventors have demonstrated that their method of tumor cell enrichment provides a cell preparation that is enriched at least 2 log, generally 3–3 log, in tumor cells. The tumor enriched cell preparations can be used to detect metastatic tumor cells in sample. Accordingly, the present invention also provides a method of detecting tumor metastasis in a sample comprising (a) reacting the sample with an antibody composition comprising antibodies specific for glycophorin A, CD2, CD14, CD16, CD38, CD45 and CD66b under conditions so that conjugates are formed between the antibodies and hematopoietic cells in the sample expressing the antigens glycophorin A, CD2, CD14, CD16, CD38, CD45 and CD66b; (b) removing the conjugates; and (c) recovering a cell preparation enriched in the tumor cells; and (d) detecting the tumor cells in the cell preparation. The tumor cells may be detected using techniques known in the art. For example, antibodies specific for tumor cells may be used in antibody mediated detection methods such as immuno-cytochemical staining (ICC).

In all of the above negative selection processes for cell enrichment, conditions which permit the formation of conjugates may be selected having regard to factors such as the nature and amounts of the antibodies in the antibody composition, and the estimated concentration of targeted cells in the sample.

The antibodies in the antibody compositions may be labelled with a marker or they may be conjugated to a matrix. Examples of markers are biotin, which can be removed by avidin bound to a support, and fluorochromes, e.g. fluorescein, which provide for separation using fluorescence activated sorters. Examples of matrices are magnetic beads, which allow for direct magnetic separation (Kernshead 19992), panning surfaces e.g. plates, (Lebkowski, J. S., et al., (1994), J. of Cellular Biochemistry supple. 18b:58), dense particles for density centrifugation (Van Vlasselaer, P., Density Adjusted Cell Sorting (DACS), A Novel Method to Remove Tumor Cells From Peripheral Blood and Bone Marrow Stem Cell Transplants. (1995) 3rd International Symposium on Recent Advances in Hematopoietic Stem Cell Transplantation-Clinical Progress, New Technologies and Gene Therapy, San Diego, Calif.), dense particles alone (Zwerner et. al., Immunol. Meth. 1996 198 (2):199–202) adsorption columns (Berenson et al. 1986, Journal of Immunological Methods 91:11–19.), and adsorption membranes. The antibodies may also be joined to a cytotoxic agent such as complement or a cytotoxin, to lyse or kill the targeted differentiated or tumors cells.

The antibodies in the antibody compositions may be directly or indirectly coupled to a matrix. For example, the antibodies in the compositions of the invention may be chemically bound to the surface of magnetic particles for example, using cyanogen bromide. When the magnetic particles are reacted with a sample, conjugates will form between the magnetic particles with bound antibodies specific for antigens on the surfaces of the differentiated cells and/or tumor cells, and the differentiated cells and/or tumor cells having the antigens on their surfaces.

Alternatively, the antibodies may be indirectly conjugated to a matrix using antibodies. For example, a matrix may be coated with a second antibody having specificity for the antibodies in the antibody composition. By way of example, if the antibodies in the antibody composition are mouse IgG antibodies, the second antibody may be rabbit anti-mouse IgG.

The antibodies in the antibody compositions may also be incorporated in antibody reagents which indirectly conjugate to a matrix. Examples of antibody reagents are bispecific antibodies, tetrameric antibody complexes, and biotinylated antibodies.

Bispecific antibodies contain a variable region of an antibody in an antibody composition of the invention, and a variable region specific for at least one antigen on the surface of a matrix. The bispecific antibodies may be prepared by forming hybrid hybridomas. The hybrid hybridomas may be prepared using the procedures known in the art such as those disclosed in Staerz & Bevan, (1986, PNAS (USA) 83:1453) and Staerz & Bevan, (1986, Immunology Today, 7:241). Bispecific antibodies may also be constructed by chemical means using procedures such as those described by Staerz et al., (1985, Nature, 314:628) and Perez et al., (1985, Nature 316:354), or by expression of recombinant immunoglobulin gene constructs.

A tetrameric immunological complex may be prepared by mixing a first monoclonal antibody which is capable of binding to at least one antigen on the surface of a matrix, and a second monoclonal antibody from the antibody composition of the invention. The first and second monoclonal antibody are from a first animal species. The first and second antibody are reacted with an about equimolar amount of monoclonal antibodies of a second animal species which are directed against the Fc-fragments of the antibodies of the first animal species. The first and second antibody may also be reacted with an about equimolar amount of the $F(ab')_2$ fragments of monoclonal antibodies of a second animal species which are directed against the Fc-fragments of the antibodies of the first animal species. (See U.S. Pat. No. 4,868,109 to Lansdorp, which is incorporated herein by reference for a description of tetrameric antibody complexes and methods for preparing same).

The antibodies of the invention may be biotinylated and indirectly conjugated to a matrix which is labelled with (strept) avidin. For example, biotinylated antibodies contained in the antibody composition of the invention may be used in combination with magnetic iron-dextran particles that are covalently labelled with (strept) avidin (Miltenyi, S. et al., Cytometry 11:231, 1990). Many alternative indirect ways to specifically cross-link the antibodies in the antibody composition and matrices would also be apparent to those skilled in the art.

In an embodiment of the invention, the cell conjugates are removed by magnetic separation using magnetic particles. Suitable magnetic particles include particles in ferrofluids and other colloidal magnetic solution. "Ferrofluid" refers to a colloidal solution containing particles consisting of a magnetic core, such as magnetite ($Fe_3O_4$) coated or embedded in material that prevents the crystals from interacting. Examples of such materials include proteins, such as ferritin, polysaccharides, such as dextrans, or synthetic polymers such as sulfonated polystyrene cross-linked with divinylbenzene. The core portion is generally too small to hold a permanent magnetic field. The ferrofluids become magnetized when placed in a magnetic field. Examples of ferrofluids and methods for preparing them are described by Kemshead J. T. (1992) in J. Hematotherapy, 1:35–44, at pages 36 to 39, and Ziolo et al. Science (1994) 257:219 which are incorporated herein by reference. Colloidal particles of dextran-iron complex are preferably used in the process of the invention. (See Molday, R. S. and McKenzie, L. L. FEBS Lett. 170:232, 1984; Miltenyi et al., Cytometry 11:231, 1990; and Molday, R. S. and MacKenzie, D., J. Immunol. Methods 52:353, 1982; Thomas et al., J. Hematother, 2:297 (1993); and U.S. Pat. No. 4,452,733, which are each incorporated herein by reference).

FIG. 1 is a schematic representation of magnetic cell labeling using tetrameric antibody complexes and colloidal dextran iron.

In accordance with the magnetic separation method, the sample containing the progenitor and stem cells to be recovered, is reacted with the above described antibody reagents, preferably tetrameric antibody complexes, so that the antibody reagents bind to the targeted differentiated cells and/or tumor cells present in the sample to form cell conjugates of the targeted differentiated cells and/or tumor cells and the antibody reagents. The reaction conditions are selected to provide the desired level of binding of the targeted differentiated cells and/or tumor cells and the antibody reagents. Preferably the sample is incubated with the antibody reagents for a period of 5 to 60 minutes at either 4° or ambient room temperature. The concentration of the antibody reagents is selected depending on the estimated concentration of the targeted differentiated cells in the sample. Generally, the concentration is between about 0.1 to 50 μg/ml of sample. The magnetic particles are then added and the mixture is incubated for a period of about 5 minutes to 30 minutes at the selected temperature. The sample is then ready to be separated over a magnetic filter device. Preferably, the magnetic separation procedure is carried out using the magnetic filter and methods described in U.S. Pat. No. 5,514,340 to Lansdorp and Thomas which is incorporated in its entirety herein by reference.

The sample containing the magnetically labelled cell conjugates is passed through the magnetic filter in the presence of a magnetic field. In a preferred embodiment of the invention, the magnet is a dipole magnet with a gap varying from 0.3 to 3.0 inches bore and having a magnetic field of 0.5–2 Telsa. The magnetically labelled cell conjugates are retained in the high gradient magnetic column and the materials which are not magnetically labelled flow through the column after washing with a buffer.

The preparation containing non-magnetically labelled cells may be analyzed using procedures such as flow cytometry. The ability of the cells in the preparation to produce colony-forming cells or long term culture initiating cells (LTCIC) in culture or repopulate SCID mice in a SCID repopulating assay (SRC) may also be assessed. The efficiency of the separation procedure may also be determined by monitoring the recovery of $CD34^+$ cells, $CD34^+CD38^-$ cells and colony forming cells.

The antibody compositions of the invention may also be used to prepare a cell preparation which is enriched for a specific differentiated cell type. This is achieved by using antibody compositions which lack antibodies to the specific differentiated cell type, in the above described processes of the invention. Particular embodiments of these processes of the invention are set out below. It will be appreciated that the markers, matrices, antibody reagents, and procedures described herein may be used in these processes to facilitate recovery of cell preparations enriched for a specific differentiated cell type. Examples of antibodies which may be used in these processes are set out in Table 3.

In accordance with one embodiment of the invention, a process is provided for enriching and recovering monocytes from a blood sample comprising reacting the sample with an antibody composition containing antibodies capable of binding to the antigens glycophorin A, CD2, CD3, CD56, and CD24 or CD19, and optionally CD66b, under conditions so that cell conjugates are formed between the antibodies and the cells in the sample having the antigens glycophorin A, CD2, CD3, CD56, and CD24 or CD19 and optionally CD66b on their surfaces; removing the cell conjugates; and recovering a cell preparation which is enriched in monocytes.

In accordance with another embodiment of the invention, a process is provided for enriching and recovering monocytes from a bone marrow sample comprising reacting the sample with an antibody composition containing antibodies capable of binding to the antigens glycophorin A, CD2, CD3, CD56, and CD24 or CD19, and optionally CD66b and/or CD66e, under conditions so that cell conjugates are formed between the antibodies and the cells in the sample having the antigens glycophorin A, CD2, CD3, CD56, and CD24 or CD19 and optionally CD66b and/or CD66e on their surfaces; removing the cell conjugates; and recovering a cell preparation which is enriched in monocytes.

In accordance with another embodiment of the invention, a process is provided for enriching and recovering B-cells from a blood sample comprising reacting the sample with an antibody composition containing antibodies capable of binding to the antigens glycophorin A, CD2, CD3, CD56, CD16 and CD14, and optionally CD66b under conditions so that cell conjugates are formed between the antibodies and the cells in the sample having the antigens glycophorin A, CD2, CD3, CD56, CD16 and CD14 and optionally CD66b on their surfaces; removing the cell conjugates; and recovering a cell preparation which is enriched in B-cells.

In accordance with another embodiment of the invention, a process is provided for enriching and recovering B-cells from a bone marrow sample comprising reacting the sample with an antibody composition containing antibodies capable of binding to the antigens glycophorin A, CD2, CD3, CD56, CD16 and CD14, and optionally CD66b and/or CD66e under conditions so that cell conjugates are formed between the antibodies and the cells in the sample having the antigens glycophorin A, CD2, CD3, CD56, CD16 and CD14 and optionally CD66b and/or CD66e on their surfaces; removing the cell conjugates; and recovering a cell preparation which is enriched in B-cells.

In accordance with another embodiment of the invention, a process is provided for enriching and recovering T-cells from a blood sample comprising reacting the sample with an antibody composition containing antibodies capable of binding to the antigens glycophorin A, CD16, CD14, CD19, CD56, and optionally CD66b under conditions so that cell conjugates are formed between the antibodies and the cells in the sample having the antigens glycophorin A, CD16, CD14, CD19, CD56, and optionally CD66b on their surfaces; removing the cell conjugates; and recovering a cell preparation which is enriched in T-cells.

In accordance with another embodiment of the invention, a process is provided for enriching and recovering T-cells from a bone marrow sample comprising reacting the sample with an antibody composition containing antibodies capable of binding to the antigens glycophorin A, CD16, CD14, CD19, CD56, and optionally CD66b and/or CD66e under conditions so that cell conjugates are formed between the antibodies and the cells in the sample having the antigens glycophorin A, CD16, CD14, CD19, CD56, and optionally CD66b and/or CD66e on their surfaces; removing the cell conjugates; and recovering a cell preparation which is enriched in T-cells.

In accordance with yet another embodiment of the invention, a process is provided for enriching and recovering $CD4^+$T-cells from a blood sample comprising reacting the sample with an antibody composition containing antibodies capable of binding to the antigens glycophorin A, CD16, CD14 CD19, CD56, CD8, and optionally CD66b, under conditions so that cell conjugates are formed between the antibodies and the cells in the sample having the antigens glycophorin A, CD16, CD14, CD19, CD56, CD8, and optionally CD66b on their surfaces; removing the cell conjugates; and recovering a cell preparation which is enriched in $CD4^+$T-cells.

In accordance with yet another embodiment of the invention, a process is provided for enriching and recovering $CD4^+$T-cells from a bone marrow sample comprising reacting the sample with an antibody composition containing antibodies capable of binding to the antigens glycophorin A, CD16, CD14 CD19, CD56, CD8, and optionally CD66b and/or CD66e, under conditions so that cell conjugates are formed between the antibodies and the cells in the sample having the antigens glycophorin A, CD16, CD14, CD19, CD56, CD8, and optionally CD66b and/or CD66e on their surfaces; removing the cell conjugates; and recovering a cell preparation which is enriched in $CD4^+$T-cells.

In accordance with a further embodiment of the invention, a process is provided for enriching and recovering $CD8^+$T-cells from a blood sample comprising reacting the sample with an antibody composition containing antibodies capable of binding to the antigens glycophorin A, CD16, CD14, CD19, CD56, CD4, and optionally CD66b under conditions so that cell conjugates are formed between the antibodies and the cells in the sample having the antigens glycophorin A, CD16, CD14, CD19, CD56, CD4, and optionally CD66b on their surfaces; removing the cell conjugates; and recovering a cell preparation which is enriched in CD8+T-cells.

In accordance with a further embodiment of the invention, a process is provided for enriching and recovering CD8+T-cells from a bone marrow sample comprising reacting the sample with an antibody composition containing antibodies capable of binding to the antigens glycophorin A, CD16, CD14, CD19, CD56, CD4, and optionally CD66b and/or CD66e under conditions so that cell conjugates are formed between the antibodies and the cells in the sample having the antigens glycophorin A, CD16, CD14, CD19, CD56, CD4, and optionally CD66b and/or CD66e on their surfaces; removing the cell conjugates; and recovering a cell preparation which is enriched in CD8+T-cells.

In accordance with a still further embodiment of the invention, a process is provided for enriching and recovering NK-cells from a blood sample comprising reacting the sample with an antibody composition containing antibodies capable of binding to the antigens glycophorin A, CD4, CD14, CD19, and CD3, and optionally CD66b under conditions so that cell conjugates are formed between the antibodies and the cells in the sample having the antigens glycophorin A, CD4 CD14, CD19, and CD3, and optionally CD66b on their surfaces; removing the cell conjugates; and recovering a cell preparation which is enriched in NK-cells.

In accordance with a still further embodiment of the invention, a process is provided for enriching and recovering NK-cells from a bone marrow sample comprising reacting the sample with an antibody composition containing antibodies capable of binding to the antigens glycophorin A, CD4 CD14, CD19, and CD3, and optionally CD66b and/or CD66e under conditions so that cell conjugates are formed between the antibodies and the cells in the sample having the antigens glycophorin A, CD4, CD14, CD19, and CD3, and optionally CD66b and/or CD66e on their surfaces; removing the cell conjugates; and recovering a cell preparation which is enriched in NK-cells.

In accordance with another embodiment, a process is provided for enriching and recovering basophils from whole blood sample comprising reacting the sample with an antibody composition containing antibodies capable of binding to the antigens glycophorin A, CD2, CD3, CD14, CD15, CD16, CD19, CD24, CD34, CD36, CD56 and CD45RA under conditions so that cell conjugates are formed between the antibodies and the cells in the sample having the antigens glycophorin A, CD2, CD3, CD14, CD15, CD16, CD19, CD24, CD34, CD36, CD56 and CD45RA on their surfaces; removing the cell conjugates; and recovering a cell preparation which is enriched in basophils.

In accordance with a further embodiment, a process is provided for enriching and recovering dendritic cells from a blood sample comprising reacting the sample with an antibody composition containing antibodies capable of binding to the antigens glycophorin A, CD3, CD14, CD16, CD19, CD34, CD56 and CD66b under conditions so that cell conjugates are formed between the antibodies and the cells in the sample having the antigens glycophorin A, CD3, CD14, CD16, CD19, CD34, CD56 and CD66b on their surfaces; removing the cell conjugates; and recovering a cell preparation which is enriched in dendritic cells. Dentritic can also be generated by culturing cells enriched for progenitors or monocytes using the previously mentioned enrichment cocktails.

In accordance with yet a further embodiment, a process is provided for enriching and recovering granulocytes from whole blood sample comprising reacting the sample with an antibody composition containing antibodies capable of binding to the antigens glycophorin A, CD2, CD56, CD19, CD14 and CD3 under conditions so that cell conjugates are formed between the antibodies and the cells in the sample having the antigens glycophorin A, CD2, CD56, CD19, CD14 and CD3 on their surfaces; removing the cell conjugates; and recovering a cell preparation which is enriched in granulocytes.

IV. Uses of the Compositions and Processes of the Invention

The compositions and processes of the invention may be used in the processing of biological samples including blood in particular, cord blood and whole blood. It has also been found that the antibody compositions of the invention can be used to prepare hematopoietic progenitor and stem cell preparations from bone marrow samples, including previously frozen bone marrow samples.

The processes of the invention are preferably used to deplete or purge erythrocytes, B and T lymphocytes, monocytes, NK cells, granulocytes, and/or tumor cells from samples to prepare hematopoietic progenitor and stem cell preparations for use in transplantation as well as other therapeutic methods that are readily apparent to those of skill in the art. For example, bone marrow or blood can be harvested from a donor in the case of an allogenic transplant and enriched for progenitor and stem cells by the processes described herein.

Using the process of the invention it is possible to recover a highly purified preparation of human hematopoietic stem/progenitor cells. In particular, a hematopoietic cell population containing greater than 50% of the hematopoietic progenitor/stem cells present in the original sample, and which is depleted of differentiated cells and/or tumor cells in the original sample by greater than 3 logarithms may be obtained. The human hematopoietic progenitor and stem cells in the preparation are not coated with antibodies, or modified making them highly suitable for transplantation and other therapeutic uses that are readily apparent to those skilled in the art.

The processes and compositions of the invention permit the isolation and recovery of mature dendritic cells and their precursors from blood (Horrocks et al., In press.). Dendritic cells have many useful applications including as antigen presenting cells capable of activating T cells both in vitro and in vivo. As an example, dendritic cells can be loaded (pulsed) in vitro with a tumor antigen and injected in vivo to induce an anti-tumor T cell response.

The cell preparations obtained using the processes of the invention may be used to isolate and evaluate factors associated with the differentiation and maturation of human hematopoietic cells. The cell preparations may also be used to determine the effect of a substance on cell growth and/or differentiation into a particular lineage.

The antibody compositions and processes of the invention may also be used to prepare a cell preparation from samples such as blood and bone marrow, which is enriched in a selected differentiated cell type. This will enable studies of specific cell to cell interactions including growth factor production and responses to growth factors. It will also allow molecular and biochemical analysis of specific cells types. Cell preparations enriched in NK cells and T-cells may also be used in immune therapy against certain malignancies.

The tumor-enriching antibody composition of the invention is adapted to enrich for tumor cells, in particular non-hematopoietic metastatic tumor cells. The composition is useful in the detection of non-hematopoietic tumor cells from blood, bone marrow, and peritoneal and pleural effusions of patients to aid in the diagnosis and detection of metastatic disease, monitoring the progression of metastatic disease, or monitoring the efficacy of a treatment. The tumor enriching antibody composition applied in one step to a sample of peripheral blood, frozen peripheral blood, or bone marrow containing tumor cells results at least a 2 log enrichment (and typically 3–4 log) of the tumor cells.

One currently used method for enriching for non-hematopoietic tumor cells is to use a negative selection technique with antibodies specific for CD45. The inventors have compared their antibody composition with anti-CD45 alone on the ability to enrich peripheral blood mononuclear cells for breast carcinoma tumor cells and have shown that the antibody composition of the invention enriches the tumor cells 10 fold (1 log) over anti-CD45 alone.

The present invention also includes a useful kit in preparing a cell preparation enriched in hematopoietic stem cells and progenitor cells comprising antibodies specific for glycophorin A, CD3, CD24, CD16, CD14 and instructions for preparing a cell preparation enriched in hematopoietic stem cells and progenitor cells.

The present invention further includes a kit useful in preparing a cell preparation enriched in hematopoietic stem and progenitor cells and depleted in hematopoietic tumor cells comprising antibodies specific for glycophorin A, CD3, CD24, CD16, CD14 and instructions for preparing a cell preparation enriched in hematopoietic stem cells and progenitor cells and depleted in hematopoietic tumor cells.

The present invention also includes a kit useful in preparing a cell preparation enriched in hematopoietic stem cells and progenitor cells and depleted in tumor cells comprising antibodies specific for glycophorin A, CD3, CD24, CD16, CD14, and an antigen present on the tumor cells and instructions for preparing a cell preparation enriched in hematopoietic stem cells and progenitor cells and depleted in tumor cells.

The present invention also relates to kits useful in preparing a preparation of non-hematopoietic tumor cells comprising antibodies specific for glycophorin A, CD2, CD14, CD16, CD38, CD45 and CD66b and instructions for performing the tumor cell enriching processes of the invention.

The following non-limiting examples are illustrative of the present invention:

EXAMPLES

Example 1

Method for Evaluating Antibody Combinations

Suspensions of normal human bone marrow, human cord blood, mobilized human peripheral blood and previously frozen human bone marrow were labelled with tetrameric antibodies and colloidal dextran iron for magnetic cell depletions. Monoclonal antibodies recognizing lineage specific cell surface antigens were mixed with a mouse $IgG_1$ anti-dextran antibody (Thomas, T. E, et al. (1992), J. Immunol Methods 154:245;252) and a rat $IgG_1$ monoclonal antibody which recognizes the Fc portion of the mouse $IgG_1$ molecule (TFL-P9) (Lansdorp, P. M, and Thomas T. E. (1990), Mol. Immunol. 27:659–666). Tetrameric antibody complexes (Lansdorp, P. M, and Thomas, T. E. (1990), Mol. Immunol. 27:659–666; U.S. Pat. No. 4,868,109 to Lansdorp) spontaneously form when mouse $IgG_1$ molecules (the lineage specific monoclonal antibody and anti-dextran) are mixed with P9. A proportion of these tetrameric antibody complexes are bifunctional, recognizing an antigen on the surface of the target cell on one side and dextran (part of the magnetic colloidal dextran iron) on the other. Tetrameric antibody complexes were made for all the antibodies in the lineage cocktail. FIG. 1 shows a schematic representation of magnetic cell labeling using tetrameric antibody complexes and colloidal dextran iron.

Cells were labelled for separation ($1–5\times10^7$ cells/ml) by incubating them with the desired combination of tetramers for 30 min on ice followed by a 30 min incubation with colloidal dextran iron (final OD450=0.6) (Molday and MacKenzie 1982, 52(3): 353–367). The cells were then passed through a magnetic filter (U.S. Pat. No. 5,514,340; inventors Lansdorp and Thomas) at 1 cm/min. The magnetically labelled cells bind to the filter and the unlabeled cells pass through. FIG. 1 shows a schematic representation of magnetic cell labeling using tetrameric antibody complexes and colloidal dextran iron.

Figure 2B:
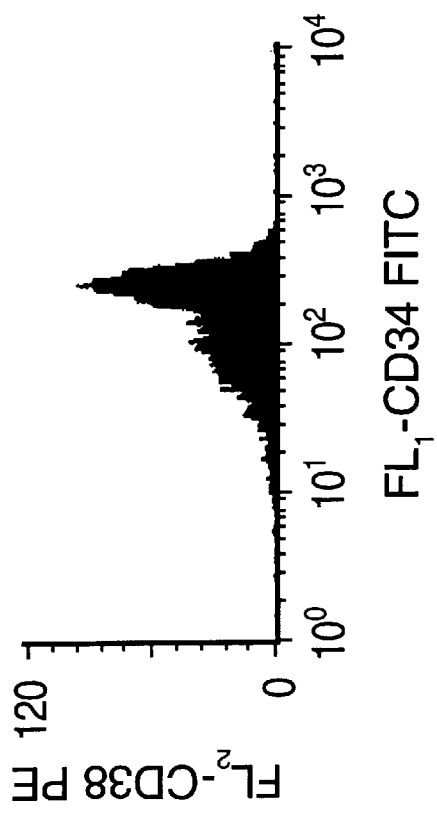
FIG. 2B shows a Fluorescence Activated Cell Sorting (FACS) histogram of mobilized peripheral blood after progenitor enrichment using the progenitor enrichment composition.
Figure 2A:
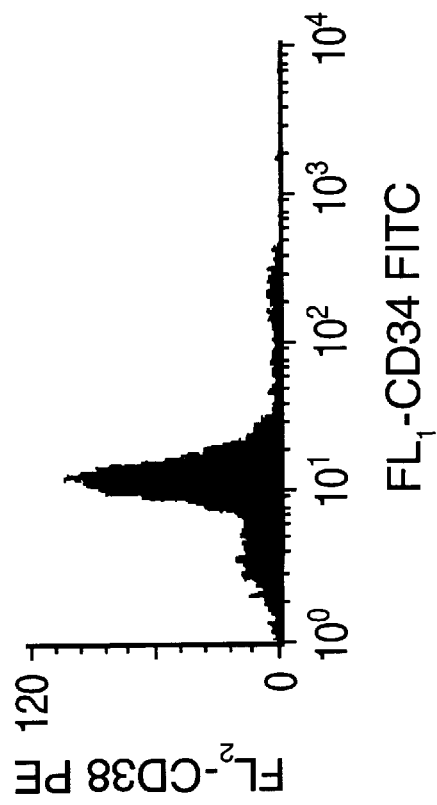
FIG. 2A shows a Fluorescence Activated Cell Sorting (FACS) histogram of mobilized peripheral blood before progenitor enrichment using the progenitor enrichment composition.

The flow through fraction is collected and analyzed for hematopoietic colony forming cells (CFU-GM, CFU-C, LTCIC) (Eaves, C. J. and Eaves, A. J. 1992 In: Current Therapy in Hematology-Oncology, Fourth Edition pp. 159–167), CD34+ cells, and CD34+ CD38– cells. The enrichment of these cell types depends on how well the antibody cocktail has targeted other cells for removal. Each antibody cocktail was evaluated for the purity and recovery of colony forming cells, CD34+ cells, and CD34+CD38– cells. FIG. 2 shows a FACS histogram of mobilized peripheral blood before and after progenitor enrichment via lineage depletion.

Example 2

Antibodies for the Enrichment of Progenitor Cells (Progenitor Cocktail)

The results of numerous cell separations identified a combination of lineage specific antibodies that produce the maximum enrichment and recovery of CD34+ cells and colony forming cells.

Targeting Erythrocytes—Anti-glycophorin A antibodies were used to label erythrocytes for depletion. Many of these antibodies will cause agglutination at moderate to high antibody concentrations (3–10 $\mu$g/ml). It was found that cells could be effectively targeted for magnetic depletion with concentrations of anti-glycophorin antibody that were several fold lower than that which caused agglutination.

Targeting Lymphocytes—B, T, and NK cells were targeted with monoclonal antibodies against CD24, CD3, CD19, CD20, CD56, CD2. Initial depletions of mobilized peripheral blood using just anti-CD24 and CD3 for lymphocyte depletion showed that a proportion of the CD34 negative cells in the purified fraction were CD56 positive (NK cells). Subsequent tests with and without anti-CD56 increased the purity of CD34+ cells in the recovered fraction by 12–20%. Adding an anti-CD2 to the cocktail increased the purity an additional 12–13%. Anti-CD2 and anti-CD56 had no significant effect on lineage depletions of fresh bone marrow. It is likely that bone marrow does not have as many CD3–CD2+ and CD3–CD56+ cells. Anti-CD2 and anti-CD56 are added to the depletion cocktails for mobilized peripheral blood but not bone marrow.

Antibodies against CD24 were sufficient to target all detectable B-cells for depletion. Adding anti-CD19 gave no additional enrichment of CD34+ cells from mobilized peripheral blood or bone marrow. Substituting CD19 for CD24 in separations of fresh bone marrow had no effect on the enrichment or recovery of CD34+ cells, hematopoietic colony forming cells and LTCIC. Replacing anti-CD24 with anti-CD20 or both anti-CD19 and anti-CD20 had no significant effect on separations of mobilized peripheral blood. An effect was seen in a separation with cord blood; when anti-CD24 was replaced with anti-CD19, the purity was decreased 21%, but recovery of CD34+ cells was increased 28%.

Targeting Mature Myeloid Cells—Monocytes were effectively targeted with an antibody against CD14 in all cell suspensions tested. The removal of granulocytes from peripheral blood and fresh bone marrow was more efficient using both anti-CD16 and anti-CD66b rather than anti-CD16 alone and adding anti-CD66e gave an additional 10% enrichment of CD34+ cells from fresh bone marrow and 20% enrichment for peripheral blood. Anti-CD16 alone was sufficient to deplete the granulocytes from previously frozen marrow. Adding anti-CD41 or CD42a did not increase the purity of CD34+ cells in either peripheral blood or bone marrow.

Example 3

Antibodies for the Enrichment of Stem Cells (Stem Cell Cocktail)

Both pluripotent stem cells and committed progenitors express CD34, but the CD34 compartment can be further subdivided using a variety of cell surface markers to isolate these cell types. Stem cells co-purify in a population of CD34+ cells which lack or have low expression of certain lineage markers (CD38, CD33, CD45RA, CD71, CD36 and HLA-DR) (Craig et al. 1994, British Journal of Haematology, 88:24–30; Lansdorp, P.AI. and Dragowska, W. 1992, J. Exp. Med. 175:1501–1509; Sutherland, H, J., et al. 1989, Blood 74.1563–1570.). If antibodies recognizing these angitens are included in the lineage cocktail one can further enrich for stem cells while losing some of the committed mature CD34+ cells. Antibodies to CD36, CD38 and CD45RA were added to the lineage cocktail to specifically enrich for stem cells. The recovery of CD34+ CD38– cells (Tables 5) and LTCICs (Table 6) were monitored to determine the efficiency of the lineage depletions with the "stem cell cocktail".

Including anti-CD45RA in the stem cell cocktail does not negate the need for anti-CD24 in the cocktail nor does anti-CD36 allow the removal of CD66e. Adding anti-CD36 did increase the purity of CD34+CD38– cells in separations of previously frozen bone marrow by 15%. The addition of anti-transferring (CD71) antibody to the cocktail resulted in very poor recovery of CD34+ CD38– cells, and LTCIC as well as producing a significant number of dead cells in the enriched fraction (viability normally >95%).

Figure 3B:
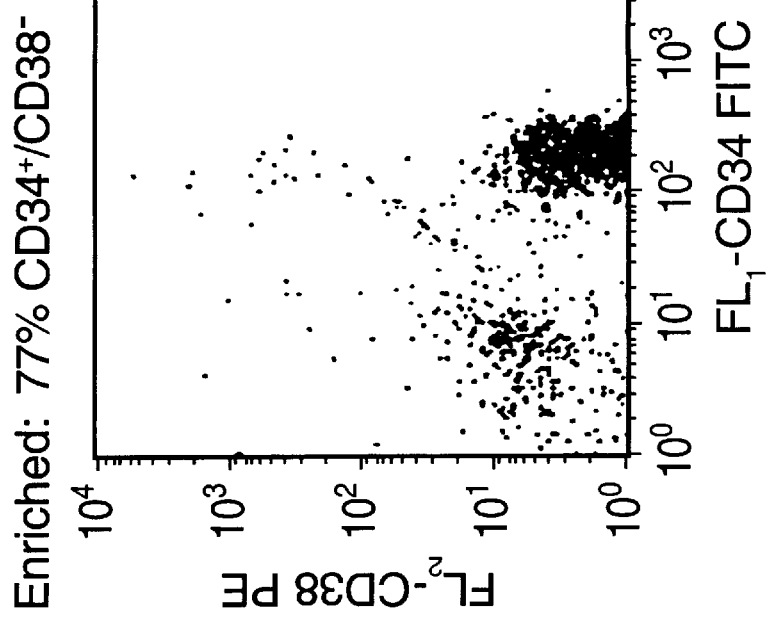
FIG. 3B shows a Fluorescence Activated Cell Sorting (FACS) profile of mobilized peripheral blood after enrichment using the primitive progenitor enrichment composition.
Figure 3A:
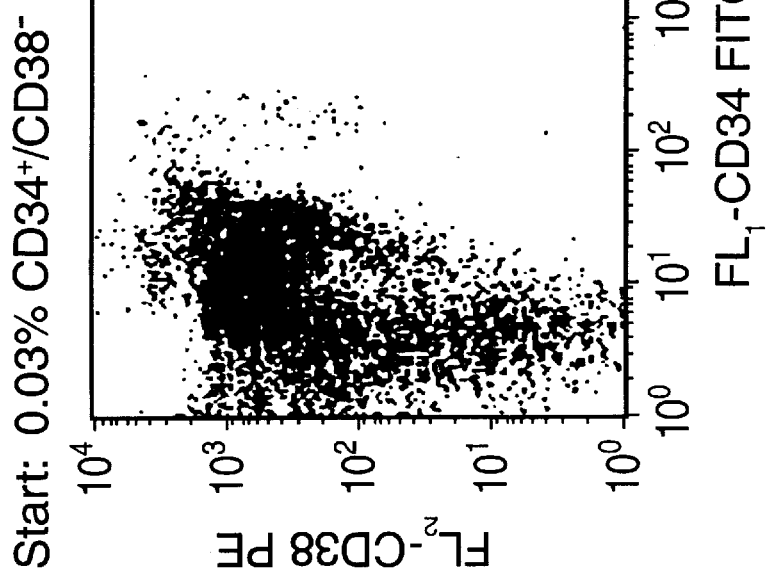
FIG. 3A shows a Fluorescence Activated Cell Sorting (FACS) profile of mobilized peripheral blood before enrichment using the primitive progenitor enrichment composition.
Figures 4A, 4B:
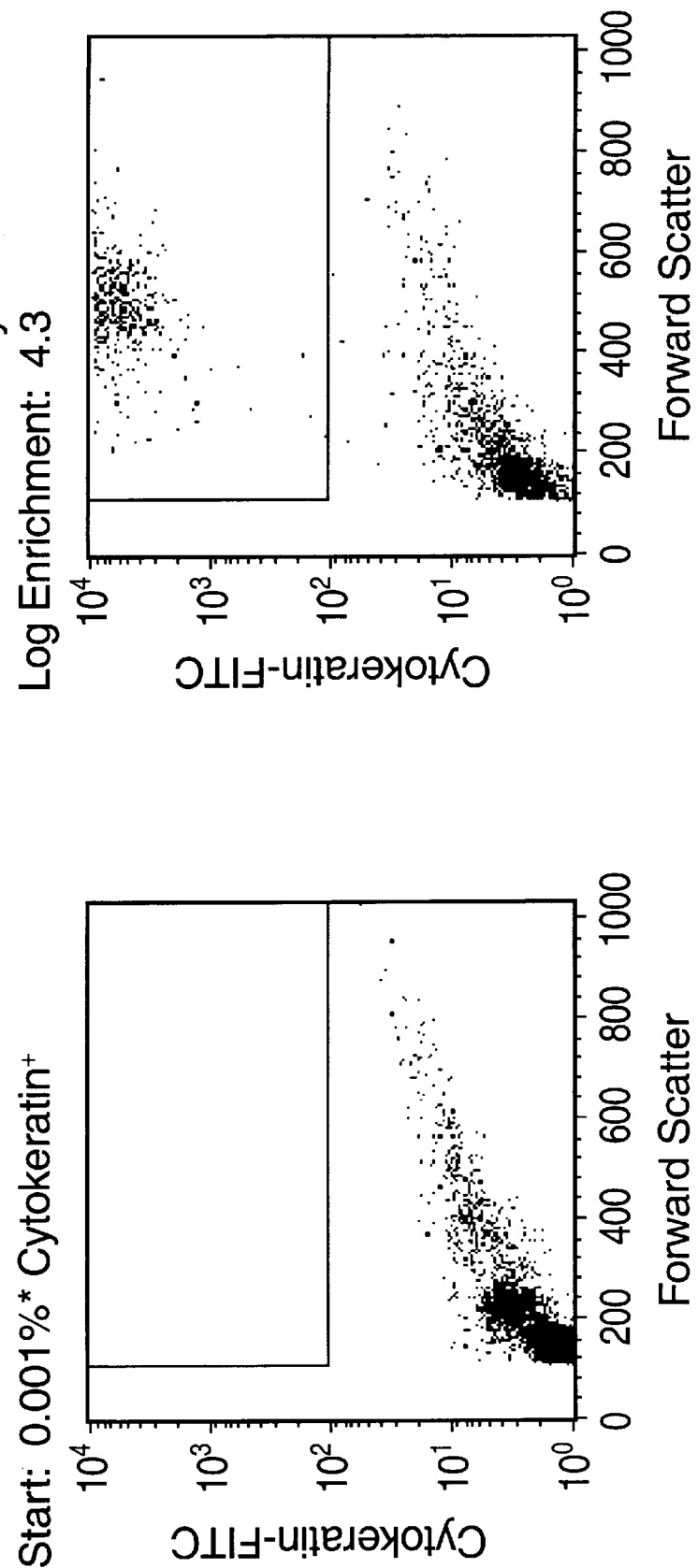
FIG. 4A shows a Fluorescence Activated Cell Sorting (FACS) profile of peripheral blood seeded with CAMA Breast carcinoma cell line before enrichment using the tumor enrichment composition.
FIG. 4B shows a Fluorescence Activated Cell Sorting (FACS) profile of peripheral blood seeded with CAMA Breast carcinoma cell line after enrichment using the tumor enrichment composition.
Figure 5B:
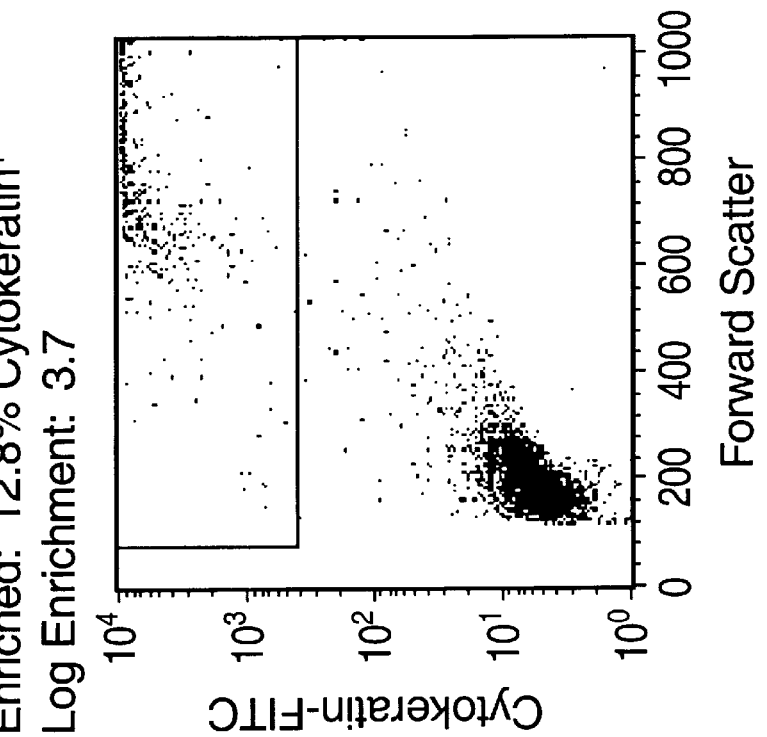
FIG. 5B shows a Fluorescence Activated Cell Sorting (FACS) profile of peripheral blood seeded with pleural effusion cells after enrichment using the tumor enrichment composition.
Figure 5A:
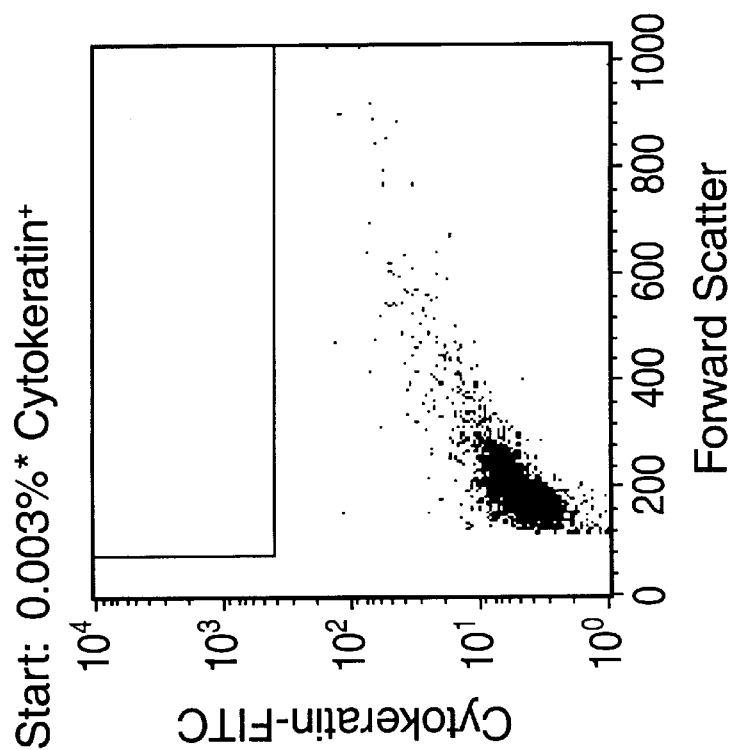
FIG. 5A shows a Fluorescence Activated Cell Sorting (FACS) profile of peripheral blood seeded with pleural effusion cells before enrichment using the tumor enrichment composition.

The results shown in Tables 5 and 6 demonstrate that separation of blood and bone marrow with the stem cell cocktail produced a cell suspension which is at least 30% and up to about 80% CD34+ CD38– with up to 90% recovery of these cells. FIG. 3 shows a FACS profile of peripheral blood before and after progenitor enrichment with the antibody cocktail.

Example 4

Different Antibodies to the Same Antigen

The enrichment of hematopoietic progenitor cells via lineage depletion is not only dependent on the number of types of committed cells that are targeted but also the effectiveness of this targeting and subsequent removal using magnetic separation or other antibody mediated techniques. It was found that different antibodies recognizing the same antigen may reproducibly produce different degrees of progenitor enrichment. The anti-CD24 antibody 32D12 produced better results in lineage depletions than ALB9 (also anti-CD24); the purity of the enriched cell suspension increased 10% in a separation with cord blood. In cell depletions with a single tetramer type, 32D12 out performed ALB9 and anti-glycophorin antibody 10F7MN out performed anti-glycophorin antibody D2.10 although switching anti-glycophorin antibodies in a lineage depletion had no significant effect.

The criteria for choosing a particular antibody at a given concentration is its performance in a magnetic cell separation which equates to the maximum depletion of antibody targeted cells with the maximum recovery of non-target cells. Often depletion of anybody targeted cells increases with antibody concentration but so does the non-specific labeling of cells. In general, the result looked for was a 3 log depletion with greater than 75% recovery of CD34+ cells for a non-targeted lymphocytes of the test cell suspension was steady state peripheral blood. The performance in a cell separation typically mimicked the degree of specific cell labeling and the degree on non-specific labeling measured by FACS (sheep anti-mouse FITC staining). Staining experiments were often run to eliminate antibodies (specific staining low, non-specific staining high) and reduce the number of antibody concentrations to be tested in cell separations.

Example 5

Purging Breast Carcinoma Cells (BT20 or T47D Cells)

Tetramers of anti-breast carcinoma antibodies as shown in Table 4 were combined with a progenitor enrichment cocktail (D2.10, UCHT1, MEM15, 3G8, ALB9, 80H3, J4.119, 6F10.3, T199, and optionally 8D2.2, T16 and FA60152, or 10F7MN, UCHT1, 32D12, MEM154, MEM15 or B13.9, T199, 6F10.3, J4.119, and optionally, 8D2.2, T16 and 1VC7) to produce a cocktail for breast carcinoma purging and debulking. Including the lineage depletion increases the degree of tumor purge over that seen with just anti-tumor antibodies alone (Table 7). Breast carcinoma cell lines were added to previously frozen marrow, peripheral blood leukapheresis or fresh bone marrow. Tumor cell purges were performed using the anti-breast carcinoma antibodies indicated in Table 7 with and without the standard lineage depletion (progenitor enrichment cocktail). The recovery of hematopoietic progenitors during lineage depletion is given in Table 8. Enrichment of progenitors was generally 50 to 100 fold.

In summary, purging tumor cells for hematopoietic progenitors in a one step selection using the antibody cocktail as indicated in Table 7 achieves a much higher degree of tumor cell purging than positive selection techniques while offering a similar degree of progenitor enrichment. The recoveries of hematopoietic progenitor cells in a lineage depletion are greater than those typically seen with positive selection.

Example 6

Enrichment of Breast Carcinoma Cells in Bone Marrow

Cells from the CAMA breast carcinoma cell line were mixed with previously frozen bone marrow (BM) and processed with the enrichment antibody composition (D2.10, UCHT1, MEM15, 3G8, 8OH3, J4119, 6F10.3, T199, 8D2.2, T16, FA6.152, and J33) in a one step magnetic depletion. The results shown in Table 9 demonstrates that the CAMA cells were enriched 2–3 log using the tumor enrichment antibody compositions.

Example 7

Enrichment of Breast Carcinoma Cells in Peripheral Blood

Cells from the CAMA breast carcinoma cell line were seeded into previously frozen peripheral blood mononuclear cells (PBMC) and processed with the enrichment antibodies capable of binding to glycophorin A (2B7.1), CD2 (6710.3), CD14 (MEM15), CD16 (3G8), CD38 (T16), CD45 (J33) and CD66b (80H3) in a one step magnetic depletion. The results shown in Table 10 demonstrate that CAMA cells were enriched up to 4.5 log.

Example 8

Comparison with Antibodies to CD45

Cells from the CAMA breast carcinoma cell line were seeded into previously frozen peripheral blood mononuclear cells (PBMC) and processed with the enrichment antibodies capable of binding to glycophorin A (2B7.1), CD2(6710.3), CD14 (MEM15), CD16 (3G8), CD38 (T16), CD45 (J33) and CD66b (80H3). The results were compared with the common method of negative selection, ie. the use of anti-CD-45 alone. The results shown in Table 11, demonstrates that there is close to a ten fold (1 log) greater enrichment using the antibody composition of the invention, over negative selection with CD45.

Example 9

Enrichment of Epithelial Tumor Cells From Pleural Effusion Samples

Pleural effusion samples were taken from patients with suspected metastatic disease. The pleural effusions were separated using the tumor enrichment composition of antibodies capable of binding to glycophorin A (2B7.1), CD2 (6710.3), CD14 (MEM15), CD16 (3G8), CD38 (T16), CD45 (J33) and CD66b (80H3). As shown in Table 12, there is up to a 2.5 log enrichment using the antibody composition of the invention.

Example 10

Enrichment of Epithelial Tumors Cells from Pleural Effusion Samples Diluted into Peripheral Blood Pleural effusion samples were taken from patients with suspected metastatic disease and seeded into previously frozen PBMC to mimic metastatic cells in the blood, and then separated using the tumor enrichment composition of antibodies capable of binding to glycophorin A (2B7.1), CD2 (6710.3), CD14 (MEM15), CD16 (3G8), CD38 (T16), CD45 (J33) and CD66b (80H3). As shown in Table 13, there is up to a enrichment using the antibody composition of the invention, with up to a 4.9 log enrichment and 95% recovery.

While what is shown and described herein constitutes various preferred embodiments of the subject invention, it will be understood that various changes can be made to such embodiments without departing from the subject invention, the scope of which is defined in the appended claims.

TABLE 1

Optimal Antibody Cocktail for the Enrichment of Hematopoietic Progenitors

| Cell Suspension | optimum antibody cocktail anti- | % purity CD34+ cells | % recovery CD34+ cells |
| --- | --- | --- | --- |
| fresh bone marrow | gly*, CD3, CD24, CD16, CD14, CD66e, CD66b, | 39, 44, 38 | 67, 48, 55 |
| previously frozen bone marrow | gly, CD3, CD24, CD16, CD14, | 64, 46, 50, 53 | 85, 55, 82, 64 |
| mobilized peripheral blood | gly, CD3, CD24, CD16, CD14, CD66e, CD66b, CD56, CD2, CD19 | 51, 50, 57 | 43, 49, 85 |
| cord blood | gly, CD3, CD24, CD16, CD14, CD66e, CD66b, CD56, CD2, CD19 | 56, 88, 58, 55, 63 | 75, 85, 53, 67, 48 |

*gly = glycophorin A

TABLE 2

Antibodies used in Lineage Depletions

| Antigen | Antibody | Source | Concentration ug/ml |
| --- | --- | --- | --- |
| glycophorin A | 10F7MN* | U.S. Pat. No. 4,752,582 | 1 |
|  | D2.10 | IMMUNOTECH, Marseille, France | 2 |
|  | 2B7.1 | StemCell Technologies | 1 |
| CD2 | 6F10.3 | IMMUNOTECH, Marseille, France | 3 |
| CD3 | UCHT1 | IMMUNOTECH, Marseille, France | 3 |
|  | SK7 | Becton Dickinson Immunocytometry, Mountain View, Calif. |  |

TABLE 2-continued

Antibodies used in Lineage Depletions

| Antigen | Antibody | Source | Concentration ug/ml |
|---|---|---|---|
| CD4 | 13B8.2 | Becton Dickinson Immunocytometry, Mountain View, Calif. | 3 |
| CD8 | B911 | Becton Dickinson Immunocytometry, Mountain View, Calif. | 3 |
|  | OKT3 | BioDesigns | 3 |
| CD14 | MEM 15 | Dr. Vaclav Horejsi, Institute of Molecular | 2 |
|  | MEM 18 | Genetics Academy of Sciences of the Czech Republic, Praha, Czech Republic; Cedarlane Laboratories Hornby, Ontario, Canada | 2 |
| CD16 | MEM 154* | Dr. Vaclav Horejsi, Institute of Molecular Genetics Academy of Sciences of the Czech Republic, Praha, Czech Republic; Cedarlane Laboratories Hornby, Ontario, Canada | 2 |
|  | 3G8 | IMMUNOTECH, Marseille, France | 3 |
|  | NKP15 | Becton Dickinson Immunocytometry, Mountain View, Calif. | 3 |
| CD19 | J4.119 | IMMUNOTECH, Marseille, France | 3 |
|  | 4G7 | Becton Dickinson Immunocytometry, Mountain View, Calif. |  |
| CD20 | MEM97 | Dr. Vaclav Horejsi, Institute of Molecular Genetics Academy of Sciences of the Czech Republic, Praha, Czech Republic; Cedarlane Laboratories Hornby, Ontario, Canada | 3 |
|  | L27 | Becton Dickinson Immunocytometry, Mountain View, Calif. | 3 |
| CD24 | 32D12* | Dr. Steinar Funderud, Institute for Cancer Research, Dept. of Immunology, Oslo, Norway | 2 |
|  | ALB9 | IMMUNOTECH, Marseille, France | 3 |
| CD36 | FA60152 | IMMUNOTECH, Marseille, France | 3 |
|  | IVC7 | CLB, Central Laboratory of the Netherlands, Red Cross Blood Transfusion Service |  |
| CD38 | T16 | IMMUNOTECH, Marseille, France | 3 |
| CD41 | PI1.64 | Kaplan, 5th International Workshop on Human Leukocyte Differentiation Antigens | 3 |
| CD42a | Beb1 | Becton Dickinson Immunocytometry, Mountain View, Calif. | 3 |
| CD45 | J33 | IMMUNOTECH, Marseille, France | 3 |
|  | MEM28 | Dr. Vaclav Horejsi, Institute of Molecular | 1 |
| CD45RA | 8D2.2 | Craig et al. 1994, StemCell Technologies, Vancouver, Canada | 1 |
|  | L48 | Becton Dickinson Immunocytometry, Mountain View, Calif. | 3 |
| CD56 | T199 | IMMUNOTECH, Marseille, France | 3 |
|  | MY31 | Becton Dickinson Immunocytometry, Mountain View, Calif. | 3 |
| CD66e | CLB/gran10 | CLB, Central Laboratory of the Netherlands, Red Cross Blood Transfusion Service | 3 |
| CD66b | B13.9 | CLB, Central Laboratory of the Netherlands, Red Cross Blood Transfusion Service | 3 |
|  | 80H3 | IMMUNOTECH, Marseille, France | 3 |

*preferred antibody based on performance in magnetic cell separations

TABLE 3

Antibody Cocktails to Purify Specific Types of Lineage Committed Cells

| Desired Cell type | source of cells | cocktail of antibodies |
|---|---|---|
| Monocytes | Ficolled Blood | anti-glycophorin A, anti-CD2, CD3, CD56, CD19 |
|  | Whole Blood | anti-glycophorin A, anti-CD2, CD3, CD56, CD19, CD66b |
| B-Cells | Ficolled Blood | anti-glycophorin A, anti-CD3, CD56, CD14, CD16, CD2 |
|  | Whole Blood | anti-glycophorin A, anti-CD3, CD56, CD14, CD66b, CD16, CD2 |
| T-Cells | Ficolled Blood | anti-glycophorin A, anti-CD19, CD56, CD16, CD14 |
|  | Whole Blood | anti-glycophorin A, anti-CD19, CD56, CD66b, CD16, CD14 |
| CD4+ T-Cells | Ficolled Blood | anti-glycophorin A, anti-CD19, CD56, CD8, CD16, CD14 |
|  | Whole Blood | anti-glycophorin A, anti-CD19, CD56, CD8, CD66b, CD16, CD14 |
| CD8+ T-Cells | Ficolled Blood | anti-glycophorin A, anti-CD19, CD56, CD4, CD16, CD14 |
|  | Whole Blood | anti-glycophorin A, anti-CD19, CD56, CD4, CD66b, CD16, CD14 |
| NK Cells | Ficolled Blood | anti-glycophorin A, anti-CD19, CD3, CD14, CD4 |
|  | Whole Blood | anti-glycophorin A, anti-CD19, CD3, CD66b, CD14, CD4 |
| Basophils | Whole Blood | anti-glycophorin A, anti-CD2, anti-CD3, anti-CD14, anti-CD15, anti-CD16, anti-CD19, anti-CD24, anti-CD34, anti-CD36, anti-CD56 and anti-CD45RA |
| Dendritic Cells | Whole Blood | anti-glycophorin A, anti-CD3, anti-CD14, anti-CD16, anti-CD19, anti-CD34, anti-CD56 and anti-CD66b |
| Granulocytes | Whole Blood | anti-glycophorin A, anti-CD2, anti-CD56, anti-CD19, anti-CD14, and anti-CD3 |

TABLE 4

Antibodies Recognizing Non-Hematopoietic Antigens Expressed on Epithelial Tumor Cells.

| Disease | Antibody | Antigen | Supplier/Developer |
| --- | --- | --- | --- |
| Breast and Lung Carcinoma | 5E11 | unknown, breast carcinoma | STI |
| | 6E7 | unknown, breast carcinoma | STI |
| | H23A | unknown, breast carcinoma | ATCC |
| | RAR9941 | epithelial glycoprotein | Baxter, Germany |
| | RAR9948 | epithelial glycoprotein | Baxter, Germany |
| | RAR9938 | crb2 | Baxter, Germany |
| | C13B5 | crb2 | Immunotech, Marseille, France |
| | BRST 1 | BCA 225 | ID Labs |
| | BRST 3 | TAG-72 | ID Labs |
| | CA15.3 | MAM-6, mucin | ID Labs |
| | CA27.29 | MAM-6, mucin | Cedarlane |
| | BcrEp4 | HEA | DAKO |
| Neuroblastoma | UJ13A | unknown | Hurko and Walsh (1983) Neurology 33:734 |
| | UJ181.4 | unknown | Hurko and Walsh (1983) Neurology 33:734 |
| | UJ223.8 | unknown | Hurko and Walsh (1983) Neurology 33:734 |
| | UJ127.11 | unknown | Hurko and Walsh (1983) Neurology 33:734 |
| | 5.1.H11 | unknown | Hurko and Walsh (1983) Neurology 33:734 |
| | 390,459 | unknown | R. C. Seeger, L.A. Children's Hospital, Calif. |
| | BA-1.2 | unknown | R. C. Seeger, L.A. Children's Hospital, Calif. |
| | HSAN 1.2 | unknown | Reynolds and Smith (1982) Hybridomas in Cancer p235 |

TABLE 5

Purity and Yield of Human CD34+ CD38− Cells Obtained Using the Primitive Progenitor Enrichment Procedure

| Cell Sample | n | % CD34+ CD38− Start Fraction | % CD34+ CD38− Enriched Fraction | % Yield CD34+ CD38− Cells |
| --- | --- | --- | --- | --- |
| Mobilized PB | 3 | 0.02 ± 0.01 | 67 ± 6 | 50 ± 5 |
| Frozen CB | 1 | 0.16 | 78 | 20 |
| BM | 3 | 0.03 ± 0.01 | 61 ± 11 | 80 ± 10 |
| Frozen BM | 6 | 0.05 ± 0.01 | 34 ± 6 | 90 ± 20 |

% CD34+ CD38− cells in start fraction are typically too low to detect accurately, therefore values given are rough estimates. Accordingly, % recovery values, which represent the present ratio of input vs. recovered absolute numbers of % CD34+ CD38*− cells, are also relatively inaccurate.

TABLE 6

Enrichment and Yield of Long-Term Culture Initiating Cells (LTC-IC) Using the Primitive Progenitor Enrichment Procedure

| Type of Cells | % Yield of LTC-IC | Fold-Enrichment of LTC-IC |
| --- | --- | --- |
| Mobilized PB | 160 | 2,000 |
| | 70 | 1,000 |
| Frozen CB | 180 | 4,000 |
| BM | 110 | 10,000 |
| | 110 | 5,500 |

TABLE 7

Purging Breast Carcinoma Cells (BT20 or T47D cells).

| Cell Type | Lineage Depletion | Anti-Breast Carcinoma Antibodies | Log Tumor Cell Depletion |
|---|---|---|---|
| Previously Frozen Bone Marrow | Purge Only | 5E11 | 1.8 |
| | | 5E11, H23A | 3.7, 3.7 |
| | | 5E11, 6E7 | 3.0 |
| Previously Frozen Bone Marrow | Lineage Depletion and Purge | 5E11 | >5.8, 3.9, 4.7 |
| | | RAR | >5.8, 4.3, 4.7 |
| | | BRST1 | 4.9 |
| | | 5E11, H23A | >5.2, 4.4 |
| | | 5E11, RAR, BRST1 | >5.8 |
| Peripheral Blood Leukapheresis | Purge only | 5E11 | 1.9, 1.9 |
| | | H23A | 1.7 |
| | | 5E11, H23A | 2.3 |
| Peripheral Blood Leukapheresis | Lineage Depletion and Purge | 5E11, H23A | 5.6 |
| Fresh Bone Marrow | Lineage Depletion and Purge | 5E11, H23A | 4.6, 4.4 |

TABLE 8

Recovery of Hematopoietic Colony Forming Cells During Lineage Depletion To Enrich For Progenitors

| Colony Assay | mean | % Recovery range |
|---|---|---|
| CFU-GM | 60–100 | 75 |
| BFU-E | 71–100 | 92 |
| LTCIC | 72–>100 | 100 |

TABLE 9

Enrichment of CAMA Breast Carcinoma Tumor Cells From Bone Marrow

| Exp # | Sample | # CAMA in Start | % CAMA in Start | % CAMA in Flow | % Recovery CAMA | Log Enrich. CAMA |
|---|---|---|---|---|---|---|
| 1 | BM | $1.1/10^2$ | 1.06 | 91.07 | 72.41 | 1.9 |
| 2 | BM | $2.2/10^2$ | 2.18 | 96.40 | 44.12 | 1.6 |
| | | $2.1/10^3$ | 0.21 | 82.16 | 75.00 | 2.6 |
| | | $2.1/10^4$ | 0.02 | 32.01 | 60.00 | 3.2 |
| 3 | BM | $2.6/10^3$ | 0.26 | 62.54 | * | 2.4 |
| | | $2.6/10^4$ | 0.026 | 11.21 | * | 2.6 |
| | | $2.6/10^5$ | 0.0026 | 2.01 | * | 2.9 |
| | | $2.6/10^6$ | 0.00026 | 0.13 | * | 2.7 |

*Cell numbers were too low to count accurately.

TABLE 10

Purity, Recovery, and Enrichment of CAMA Breast Carcinoma Tumor Cells Seeded into Previously Frozen Peripheral Blood Mononuclear Cells

| Start | Enriched Fraction | | |
|---|---|---|---|
| % Purity | % Purity | % Recovery | Log Enrichment |
| 0.3 | 95.5 | 9.0 | 2.5 |
| 0.03 | 65.3 | 13.3 | 3.4 |
| 0.003 | 17.1 | 12.1 | 3.8 |
| 0.3 | 96.7 | 14.3 | 2.5 |
| 0.03 | 52.4 | 13.1 | 3.3 |
| 0.003 | 82.7 | 14.8 | 4.5 |
| 0.3 | 92.7 | 25.8 | 2.5 |
| 0.03 | 61.4 | 17.0 | 3.3 |
| 0.003 | 16.8 | 7.0 | 3.7 |
| 0.3 | 91.2 | 14.5 | 2.5 |
| 0.03 | 61.3 | 17.9 | 3.3 |
| 0.003 | 18.0 | 8.0 | 3.8 |
| 0.02 | 24.5 | 47.2 | 3.1 |
| 0.02 | 9.3 | 42.9 | 2.7 |
| 0.1 | 97.7 | 85.8 | 2.9 |
| 0.01 | 81.0 | 86.1 | 3.9 |
| 0.001 | 21.4 | 62.1 | 4.3 |
| 0.004 | 6.6 | 4.4 | 3.2 |

TABLE 10-continued

Purity, Recovery, and Enrichment of CAMA Breast Carcinoma Tumor Cells Seeded into Previously Frozen Peripheral Blood Mononuclear Cells

| Start | Enriched Fraction | | |
|---|---|---|---|
| % Purity | % Purity | % Recovery | Log Enrichment |
| 0.03 | 42.8 | 12.5 | 3.2 |
| 0.02 | 35.7 | 12.8 | 3.3 |
| 0.01 | 40.4 | 62.3 | 3.5 |
| 0.01 | 36.3 | 54.2 | 3.4 |
| 0.01 | 33.7 | 53.0 | 3.4 |
| 0.02 | 43.3 | 25.2 | 3.4 |
| 0.02 | 52.9 | 38.1 | 3.5 |
| 0.02 | 26.9 | 113.0 | 3.2 |
| 0.02 | 34.7 | 71.9 | 3.3 |

TABLE 11

Purity and Enrichment of CAMA Breast Carcinoma Tumor Cells Seeded into Previously Frozen Peripheral Blood Mononuclear Cells: Antibody Composition of the Invention vs. CD45 Depletion Only

| | Start | Enriched Fraction | |
|---|---|---|---|
| Cocktail | % Purity | % Purity | Log Enrichment |
| Antibody Cocktail | 0.001 | 21.4 | 4.3 |
| Anti-CD45 only | 0.001 | 6.2 | 3.8 |
| Antibody Cocktail | 0.03 | 42.8 | 3.2 |
| Anti-CD45 only | 0.03 | 6.6 | 2.4 |
| Antibody Cocktail | 0.02 | 35.7 | 3.3 |
| Anti-CD45 only | 0.02 | 5.4 | 2.4 |
| Antibody Cocktail | 0.01 | 40.4 | 3.5 |
| Anti-CD45 only | 0.01 | 11.8 | 3.0 |
| Antibody Cocktail | 0.01 | 36.3 | 3.4 |
| Antibody Cocktail | 0.01 | 33.7 | 3.4 |
| Anti-CD45 only | 0.01 | 8.0 | 2.8 |
| Antibody Cocktail | 0.02 | 43.3 | 3.4 |
| Anti-CD45 only | 0.02 | 20.1 | 3.1 |
| Antibody Cocktail | 0.02 | 26.9 | 3.2 |
| Antibody Cocktail | 0.02 | 34.7 | 3.3 |
| Anti-CD45 only | 0.02 | 3.5 | 2.3 |

TABLE 12

Purity, Recovery, and Enrichment of Cytokeratin+ Cells from Pleural Effusions

| | Start | Enriched Fraction | | |
|---|---|---|---|---|
| Sample # | % Purity | % Purity | % Recovery | Log Enrichment |
| 1 | 0.3 | 85.9 | 22.5 | 2.5 |
| 2 | 1.5 | 84.0 | 10.0 | 1.8 |
| 3 | 4.4 | 56.2 | 24.8 | 1.1 |
| 4 | 2.9 | 94.4 | 14.9 | 1.5 |
| 5 | 2.8 | 87.7 | 21.2 | 1.5 |
| 6 | 19.5 | 35.4 | 67.5 | 0.3 |
| 7 | 17.4 | 99.6 | 11.7 | 0.8 |
| 8 | 0.3 | 57.6 | 6.9 | 2.2 |
| 9 | 2.1 | 93.4 | 9.2 | 1.6 |
| 10 | 0.3 | 16.7 | 0.5 | 1.8 |
| 11 | 3.7 | 91.8 | 7.6 | 1.4 |
| 12 | 2.3 | 86.5 | 61.7 | 1.6 |
| 13 | 0.0 | 3.6 | | |
| 14 | 12.3 | 82.2 | 14.8 | 0.8 |
| 15 | 74.6 | 94.5 | 8.6 | 0.1 |

TABLE 13

Purity, Recovery, and Enrichment of Cytokeratin+ Cells from Pleural Effusions Seeded into Previously Frozen Peripheral Blood Mononuclear Cells

| Start | Enriched Fraction | | |
|---|---|---|---|
| Frequency | % Purity | % Purity | % Recovery | Log Enrichment |
| $3/10^5$ | 0.003 | 16.3 | 44.6 | 3.8 |
| $3/10^6$ | 0.003 | 2.4 | 42.3 | 3.9 |
| $9/10^6$ | 0.0009 | 12.6 | 28.0 | 4.2 |
| $9/10^7$ | 0.00009 | 0.8 | 8.6 | 3.9 |
| $1/10^5$ | 0.001 | 10.2 | 19.4 | 4.0 |
| $1/10^6$ | 0.0001 | 1.4 | 31.6 | 4.2 |
| $2/10^5$ | 0.0002 | 1.7 | 44.7 | 4.0 |
| $2/10^7$ | 0.00002 | 1.1 | 95.1 | 4.8 |
| $2/10^7$ | 0.00002 | 1.3 | 31.3 | 4.9 |

We claim:

1. A negative selection process for enriching and recovering non-hematopoietic tumor cells from a sample containing non-hematopoietic tumor cells and hematopoietic cells, said process comprising (a) reacting the sample with an antibody composition containing antibodies capable of binding to the antigens glycophorin A, CD2, CD14, CD16, CD38, CD45 and CD66b, under conditions so that conjugates are formed between the antibodies and the hematopoietic cells in the sample containing the antigens glycophorin A, CD2, CD14, CD16, CD38, CD45 and CD66b on their surfaces;

(b) removing the conjugates; and (c) recovering a cell preparation which is enriched in tumor cells.

2. A process according to claim 1 wherein the antibody composition further comprises antibodies specific for CD3, CD36, CD56 or CD66e.

3. A process according to claim 1, wherein the antibodies in the antibody composition are monoclonal antibodies.

4. A process according to claim 1, wherein the antibodies in the antibody composition are labelled with a marker or they are conjugated to a matrix.

5. A process according to claim 2, wherein the antibodies in the antibody composition are labelled with biotin or a fluorochrome.

6. A process according to claim 4, wherein the matrix is magnetic beads, a panning surface, dense particles for density centrifugation, an adsorption column, or an adsorption membrane.

7. A process according to claim 6, wherein each of the antibodies in the antibody composition is incorporated in a tetrameric antibody complex which comprises a first animal species from the antibody composition containing antibodies capable of binding to the antigens glycophorin A, CD2, CD14, CD16, CD38, CD45 and CD66b, and a second antibody of the first animal species which is capable of binding to at least one antigen on the surface of a matrix, which have been conjugated to form a cyclic tetramer with two monoclonal antibodies of a second animal species directed against the Fc-fragments of the antibodies of the first animal species.

8. A process according to claim 1 wherein the tumor cells are metastatic tumor cells derived from an epithelial cancer.

9. A process according to claim 8 wherein the epithelial cancer is selected from the group consisting of lung carcinoma, breast carcinoma, colon carcinoma, prostate carcinoma and bladder carcinoma.

10. A process according to claim 1 wherein the tumor cells are enriched at least one log.

11. A process according to claim 1 wherein the sample is blood, bone marrow, pleural effusion or peritoneal effusion.

* * * * *